US012620065B2

(12) United States Patent
Stamatas et al.

(10) Patent No.: US 12,620,065 B2
(45) Date of Patent: May 5, 2026

(54) SYSTEMS AND METHODS FOR AUTOMATIC CELL IDENTIFICATION USING IMAGES OF HUMAN EPITHELIAL TISSUE STRUCTURE

(71) Applicants: Kenvue Brands LLC, Summit, NJ (US); Inria (Institut national de recherche en informatique et en automatique), Les Chesnay-Cedex (FR)

(72) Inventors: Georgios N. Stamatas, Issy-les-Moulineaux (FR); Imane Lboukili, Issy-les-Moulineaux (FR); Xavier Descombes, Sophia Antipolis Cedex (FR)

(73) Assignees: Kenvue Brands LLC, Summit, NJ (US); Inria (Institut national de recherche en informatique et en automatique), Les Chesnay-Cedex (FR)

( * ) Notice: Subject to any disclaimer, the term of this patent is extended or adjusted under 35 U.S.C. 154(b) by 365 days.

(21) Appl. No.: 18/421,230

(22) Filed: Jan. 24, 2024

(65) Prior Publication Data

US 2024/0281935 A1    Aug. 22, 2024

Related U.S. Application Data

(60) Provisional application No. 63/447,374, filed on Feb. 22, 2023.

(51) Int. Cl.
    *G06T 5/60*        (2024.01)
    *G06T 5/20*        (2006.01)
    (Continued)

(52) U.S. Cl.
    CPC ................. *G06T 5/60* (2024.01); *G06T 5/20* (2013.01); *G06T 5/70* (2024.01); *G06T 7/0016* (2013.01);
    (Continued)

(58) Field of Classification Search
    CPC .... G06T 5/60; G06T 7/73; G06T 5/70; G06T 5/20; G06T 7/0016; G06T 7/60;
    (Continued)

(56) References Cited

U.S. PATENT DOCUMENTS 8,330,807 B2    12/2012    Chen et al.
8,649,589 B2    2/2014    Gareau
(Continued)

OTHER PUBLICATIONS

Benasci et al., Geometrical and topological analysis of in vivo confocal microscopy images reveals dynamic maturation of epidermal structures during the first years of life, J Biomed Optics 20(9), 095004, 2015.
(Continued)

*Primary Examiner* — Syed Haider

(74) *Attorney, Agent, or Firm* — Samuel J. Gee

(57)    ABSTRACT

Systems and methods for improving the image quality of images of epithelial tissue structures are disclosed. The systems include training a first cycle-GAN model and a second cycle-GAN model simultaneously, where the first cycle-GAN model is trained to remove noise from an image and the second cycle-GAN model is trained to learn the structure of the image. Additional systems and methods include deploying the trained cycle-GAN model to identify an unknown image segment and/or generate a protocol for following the identified skin care treatment recommendation for an identified image segment.

7 Claims, 9 Drawing Sheets

(51) Int. Cl.

| | |
|---|---|
| *G06T 5/70* | (2024.01) |
| *G06T 7/00* | (2017.01) |
| *G06T 7/60* | (2017.01) |
| *G06T 7/73* | (2017.01) |
| *G06T 11/00* | (2006.01) |
| *G16H 30/40* | (2018.01) |
| *G06V 10/774* | (2022.01) |

(52) U.S. Cl.

CPC .................. *G06T 7/60* (2013.01); *G06T 7/73* (2017.01); *G06T 11/00* (2013.01); *G16H 30/40* (2018.01); *G06T 2207/10056* (2013.01); *G06T 2207/10064* (2013.01); *G06T 2207/10088* (2013.01); *G06T 2207/10101* (2013.01); *G06T 2207/20021* (2013.01); *G06T 2207/20081* (2013.01); *G06T 2207/20084* (2013.01); *G06T 2207/30024* (2013.01); *G06T 2207/30088* (2013.01); *G06V 10/774* (2022.01)

(58) Field of Classification Search

CPC ........... G06T 11/00; G06T 2207/10056; G06T 2207/10064; G06T 2207/10088; G06T 2207/10101; G06T 2207/20021; G06T 2207/20081; G06T 2207/20084; G06T 2207/30024; G06T 2207/30088; G16H 30/40; G06V 10/774

See application file for complete search history.

(56) References Cited

U.S. PATENT DOCUMENTS

| | | | |
|---|---|---|---|
| 11,090,393 B2 | 8/2021 | Bensaci et al. | |
| 11,298,072 B2 | 4/2022 | Dascalu | |
| 11,544,880 B2 | 1/2023 | Park et al. | |
| 2003/0148295 A1 | 8/2003 | Wan et al. | |
| 2007/0038384 A1 | 2/2007 | Kirk et al. | |
| 2007/0238941 A1 | 10/2007 | Nikolovski et al. | |
| 2009/0292027 A1 | 11/2009 | Ruvolo et al. | |
| 2010/0292543 A1 | 11/2010 | Levitt et al. | |
| 2017/0076448 A1* | 3/2017 | Chen ........................ | G06T 7/12 |
| 2019/0333219 A1* | 10/2019 | Xu .......................... | G06T 12/30 |
| 2022/0156522 A1 | 5/2022 | Shechtman et al. | |
| 2022/0309672 A1* | 9/2022 | Cherian ................. | G06N 3/094 |
| 2022/0318956 A1* | 10/2022 | Xu ........................... | G06T 5/70 |
| 2022/0383496 A1 | 12/2022 | D'Amelio | |
| 2023/0043409 A1* | 2/2023 | Afrasiabi ................ | G06F 30/27 |
| 2024/0112341 A1* | 4/2024 | Wang .................... | G06T 7/0014 |
| 2024/0119746 A1* | 4/2024 | Liu ........................... | G06T 7/11 |
| 2025/0292597 A1* | 9/2025 | Ben Hadj .............. | G06V 10/82 |

OTHER PUBLICATIONS

Cork MJ (1997) The importance of skin barrier function. Journal of Dermatological Treatment; 8: Suppl 1, S7-S13.

Crawshaw, M.; "Multi-Task Learning with Deep Neural Networks: A Survey" (2020) doi:10.48550/arXiv.2009.09796, pp. 1-43.

A.Csikász-Nagy et al., "Cooperation and competition in the dynamics of tissue architecture during homeostasis and tumorigenesis," Semin. Cancer Biol. 23(4), 293-298 (2013).

Gareau, Automated identification of epidermal keratinocytes in reflectance confocal microscopy, Journal of Biomedical Optics, 16(3): Mar. 2011: 030502-1 to 030502-3.

Gawkrodger DJ (2007) Dermatology: An Illustrated Colour Text. Edinburgh: Churchill Livingstone.

Guillaud et al., "Quantitative architectural analysis of bronchial intraepithelial neoplasia," Proc. SPIE 3921, Optical Diagnostics of Living Cells III, (Apr. 27, 2000). https://doi.org/10.1117/12.384231.

Guillaud et al., Quantitative Histopathological Analysis of Cervical Intra-Epithelial Neoplasia Sections: Methodological Issues, Cellular Oncology. More, 26 (2004) 31-43.

Holden C et al (2002) Advised best practice for the use of emollients in eczema and other dry skin conditions. Journal of Dermatological Treatment; 13: 3, 103-110.

Nehal et al., Skin Imaging With Reflectance Confocal Microscopy, Semin Cutan Med Surg 27:37-43 © 2008 Elsevier Inc.

Rudy SJ and Parham-Vetter PC (2003) Percutaneous absorption of topically applied medication. Dermatology Nursing; 15: 2, 145-152.

Schmidt U., et al., Cell Detection with Star-convex Polygons, arXiv:1806.03535 [cs.CV] (2018), pp. 265-273.

Stamatas et al., Development of a non-invasive optical method for assessment of skin barrier to external penetration, Biomedical Optics and 3D Imaging OSA (2012).

Stamatas et al., Infant skin microstructure assessed in vivo differs from adult skin in organization and at the cellular level, Pediatr Dermatol 27(2), 125-131, 2010.

I. Lboukili, G. Stamatas, and X. Descombes, "Automatic cell identification and analysis on in vivo reflectance confocal microscopy images of the human epidermis," in SPIE Photonics Europe 2022, Strasbourg, France (2022) [doi:10.1117/12.2626777].

Jiafu Wang, Min Yang, Li Yang, Yun Zhang, Jing Yuan, Qian Liu, Xiaohua Hou, Ling Fu, A Confocal Endoscope for Cellular Imaging, Engineering, vol. 1, Issue 3, 2015, pp. 351-360, ISSN 2095-8099, https://doi.org/10.15302/J-ENG-2015081. (https://www.sciencedirect.com/science/article/pii/S2095809916300121).

J. Kamarainen, "Gabor features in image analysis," 2012 3rd International Conference on Image Processing Theory, Tools and Applications (IPTA), 2012, pp. 13-14, doi: 10.1109/IPTA.2012.6469502.

Zhu et al., Unpaired Image-to-Image Translation using CycleConsistent Adversarial Networks, in IEEE International Conference on Computer Vision (ICCV), 201, pp. 2223-2232.

Brownlee, A Gentle Introduction to CycleGAN for Image Translation, Generative Adversarial Networks (2019) pp. 1-27.

Iqbal Ahmed, et al., Generative adversarial networks and its applications in the biomedical image segmentation: a comprehensive survey; International Journal of Multimedia Information Retrieval, vol. 11, No. 3 (Jul. 8, 2022), pp. 333-368.

Kim Minsu, et al., Weakly-Supervised Defect Segmentation on Periodic Textures Using CycleGAN, IEEE /Access, IEEE, USA, vol. 8 (Sep. 18, 2020), pp. 176202-176216.

Lboukili Imane, Analysis and characterization of the tissue structure of the epidermis from confocal imaging, (Dec. 8, 2023), pp. 1-167.

LBoukili Imane, et al., Automating refelctance confocal microscopy image analysis for dermatological research: a review, Journal of Biomedical Optics, SPIE, vol. 27, No. 7 (Jul. 1, 2022), p. 70902.

Invitation to Pay—JCO6306WOPCT1—PCT/IB2024/050675, Dated: Mar. 12, 2024.

International Search Report; PCT/IB2024/050675—Dated May 15, 2024, 26 pages.

Zhu Jun-Yan et al.: "Unpaired 1-7 Image-to-Image Translation Using Cycle-Consistent Adversarial Networks", 2017 IEEE International Conference on Computer Vision (ICCV), IEEE, Oct. 22, 2017 (Oct. 22, 2017), pp. 2242-2251, XP033283087, DOI: 10.1109/ICCV.2017.244.

Sheng-Ting Tsai: "H&E-like staining of 8-14 OCT images of human skin via generative adversarial network", Applied Physics Letters, vol. 121, No. 13, Sep. 28, 2022 (Sep. 28, 2022), XP093156554, 2 Huntington Quadrangle, Melville, NY 11747 ISSN: 0003-6951, DOI: 10.1063/5.0122965.

Cheng Lu: "Efficient epidermis segmentation for whole slide skin histopathological images", 2014 36th Annual International Conference of the IEEE Engineering in Medicine and Biology Society, vol. 2014, Jan. 1, 2014 (Jan. 1, 2014), pp. 5546-5549, XP093156833, United States DOI: 10.1109/EMBC.2014.6944883.

\* cited by examiner

600

605

610

SYSTEMS AND METHODS FOR AUTOMATIC CELL IDENTIFICATION USING IMAGES OF HUMAN EPITHELIAL TISSUE STRUCTURE

CROSS-REFERENCE TO RELATED APPLICATIONS

This application claims priority under 35 U.S.C. § 119(e) to U.S. Provisional Application No. 63/447,374 filed on Feb. 22, 2023, which is incorporated herein by reference in its entirety.

TECHNICAL FIELD

The present disclosure relates generally to systems and methods for analysis of images of human epithelial tissue structure. More specifically, the present disclosure relates to automatically identifying cells and features of cells by executing parallel models that remove noise from images while maintaining the position and integrity of cell membranes.

BACKGROUND

Human skin is a complex, multi-layered and dynamic system that provides a protective covering defining the interactive boundary between an organism and the environment. It is the largest organ of the body and is vitally important to our health. Skin comprises three principal layers, the epidermis, the basement membrane also known as the dermis and a layer of subcutaneous fat also known as the hypodermis. The epidermis is in contact with the external environment and protects the body from dehydration and external aggression, whether chemical, mechanical, physical, or infectious, prevents the loss of water, and maintains internal homeostasis. The dermis provides the epidermis with mechanical support and is a nurturing element of the skin.

Accurate segmentation and identification of epidermal cells on reflectance confocal microscopy (RCM) images is important in the study of epidermal architecture and topology of both healthy and diseased skin. Current methods of analysis of RCM images include performing this process manually, which is time-consuming, subject to human error and inter-expert interpretation, or are hindered by low image quality due to noise and heterogeneity, which fail to either accurately recognize and localize cells and/or the morphological features of the cells, such as keratinocytes. Thus, there is a need for improved systems and methods that identify cells using images of human epithelial tissue structures.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Various examples of the present disclosure provide systems and methods as described herein.

In one example, a computer-implemented method is provided. The computer-implemented method includes training a first cycle-GAN model, wherein the first cycle-GAN model comprises a first generator GB2A, a second generator GA2B, a first discriminator DA, and a second discriminator DB1. Training the first cycle-GAN model comprises receiving, by the first generator GB2A, a real image as a first input, generating, by the first generator GB2A, a first synthetic image as a first output, receiving, by the first discriminator DA, the real image and the first synthetic image from the first generator GB2A, informing, by the first discriminator DA, a likelihood of each of the real image and the first synthetic image as being real or synthetic, receiving, by the second generator GA2B, the real image and the first synthetic image, generating, by the second generator GA2B, a first filtered synthetic image, receiving, by the second discriminator DB1, the real image and the first filtered synthetic image from the second generator GA2B, and informing, by the second discriminator DB1, a likelihood of each of the real image and the first filtered synthetic image as being real or synthetic, wherein the first cycle-GAN model learns noise through learning a translation from the first real image towards binary segmentations. The computer-implemented method further includes training a second cycle-GAN model, wherein the second cycle-GAN model comprises a first generator GC2B, a second generator GB2C, a first discriminator DC, and a second discriminator DB2. Training the second cycle-GAN model comprises receiving, by the first generator GC2B, a Gabor-filtered image as a second input, generating, by the first generator GC2B, a second synthetic image as a second output, receiving, by the first discriminator DC, the Gabor-filtered and the second synthetic image from the first generator GC2B, informing, by the first discriminator DC, a likelihood of each of the Gabor-filtered and the second synthetic image as being Gabor-filtered or synthetic, receiving, by the second generator GB2C, the Gabor-filtered image and the second synthetic image, generating, by the second generator GB2C, a second filtered synthetic image, receiving, by the second discriminator DB2, the Gabor-filtered image and the second filtered synthetic image from the second generator GB2C, and informing, by the second discriminator DB2, a likelihood of each of the Gabor-filtered image and the second filtered synthetic image as being Gabor-filtered or synthetic, wherein the second cycle-GAN model learns a structure of at least one of the real image or the Gabor-filtered image through learning a translation from the Gabor-filtered image towards binary segmentation.

In one example, a system is provided. The system includes a memory, a processor coupled to the memory, a trained cycle-GAN model, implemented on the processor, configured to determine an epithelial tissue structure in a real image, an image generator, implemented on the processor, configured to generate an improved epithelial tissue structure image based on the determined epithelial tissue structure, and an image analyzer implemented on the processor. The image analyzer is configured to determine, by comparing a first unknown image segment to the generated improved epithelial tissue structure image, a first degree of match between the first unknown image segment and the generated improved epithelial tissue structure image, wherein the first unknown image segment is an image segment of an area of skin, in response to an application of a skin treatment regimen, ingredient, or composition to the area of the skin for a period of time, compare a second unknown image segment to the generated improved epithelial tissue structure image, and determine, based on the comparison, a second degree of match between the second unknown image segment and the generated improved epithelial tissue structure image.

In one example, one or more non-transitory computer readable medium storing instructions is provided. The instructions, when executed by a processor, cause the processor to receive user-specific information, wherein the user-specific information includes an unknown image segment of interest, and wherein the image segment of interest is analogous to a known epidermal tissue structure model image segment generated by a trained cycle-GAN model; determine, by comparing the unknown image segment to a known epidermal tissue structure model image segment, a degree of match between the unknown segment and the known epidermal tissue structure model image segment; access a data structure containing information reflecting relationships between categories of the received user-specific information and skin care treatment information, wherein the information reflects relationships derived from known epidermal tissue structure model image segments for skin care treatment; compare the received user-specific information with the accessed data; identify, based on the comparison, a skin care treatment recommendation for a user associated with the received user-specific information; generate a protocol for following the identified skin care treatment recommendation; and output the generated protocol.

Other technical features may be readily apparent to one skilled in the art from the following figures, descriptions, and claims.

BRIEF DESCRIPTION OF THE DRAWINGS

For a more complete understanding of this disclosure and its advantages, reference is now made to the following description, taken in conjunction with the accompanying drawings, in which like reference numerals reference like parts. The drawings may not be to scale.

DETAILED DESCRIPTION

Figure 1A:
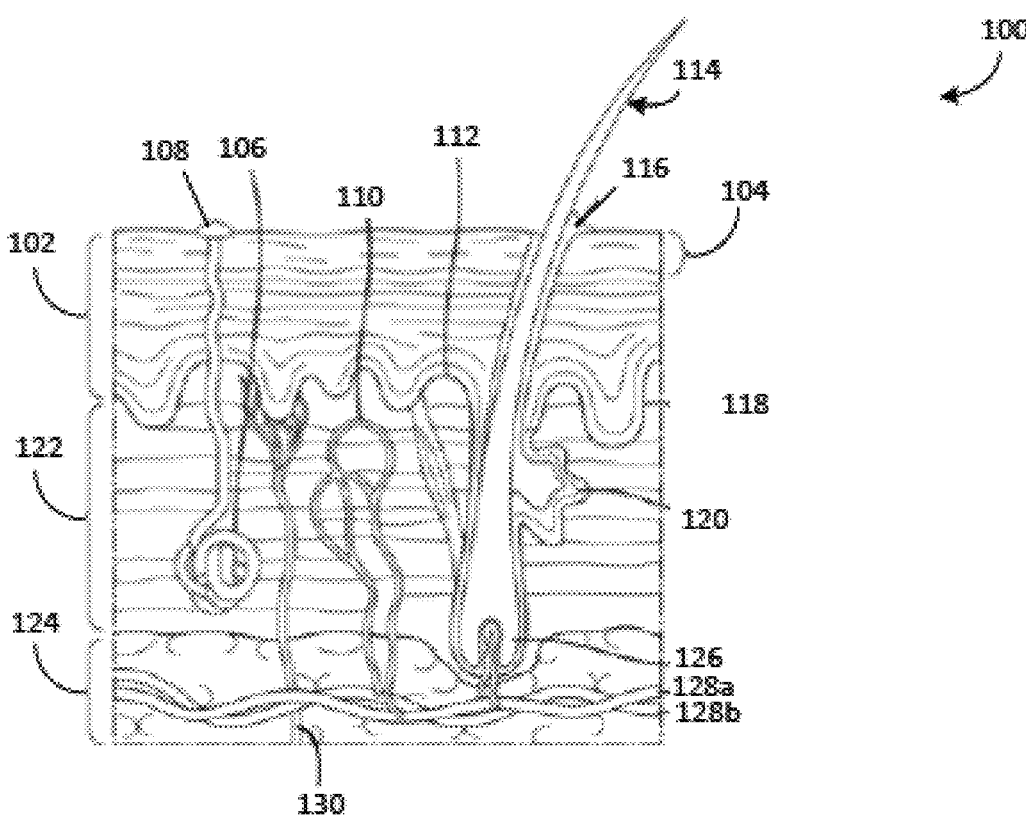
FIGS. 1A and 1B are diagrams illustrating examples of human skin.

The various implementations and examples will be described in detail with reference to the accompanying drawings. Wherever possible, the same reference numbers will be used throughout the drawings to refer to the same or like parts. References made throughout this disclosure relating to specific examples and implementations are provided solely for illustrative purposes but, unless indicated to the contrary, are not meant to limit all examples.

As used herein, the term "adversarial learning" refers to a machine-learning algorithm (e.g., generative adversarial network or adversarial discrimination neural network) where opposing learning models are learned together. For example, a "generative adversarial neural network" (or simply "generative adversarial network" (GAN)) includes a generator network and a discriminator network (e.g., an "adversarial discrimination neural network"). In particular, the term "adversarial learning" includes solving a plurality of learning tasks in the same model (e.g., in sequence or in parallel) while utilizing the roles and constraints across the tasks. A "cycle-GAN" is an unsupervised network for unpaired image-to-image translation using a GAN model architecture. It uses two unrelated collections of images composed of two types of models: 2 generators and 2 discriminators. The generator takes an image as input and generates an image from the target domain. The discriminator predicts whether the image is real (from one of the datasets) or fake (created by the generator).

The two models, the generator and discriminator, are trained together. A single training cycle involves first selecting a batch of real images from the problem domain. A batch of latent points is generated and fed to the generator model to synthesize a batch of images. The discriminator is then updated using the batch of real and generated images, minimizing binary cross-entropy loss used in any binary classification problem. The generator is then updated via the discriminator model. This means that generated images are presented to the discriminator as though they are real (not generated) and the error is propagated back through the generator model. This has the effect of updating the generator model toward generating images that are more likely to fool the discriminator. This process is then repeated for a given number of training iterations. The two models are trained together in a zero-sum game, adversarial, until the discriminator model is fooled about half the time, meaning the generator model is generating plausible examples.

A "binary image" is one that consists of pixels that can have one of exactly two colors, usually black and white. The term "capturing (an image)", or any form thereof, refers to the use of an image capture device to acquire an image. As used herein, the term "digital image" or "image" refers to any digital symbol, picture, icon, or illustration. For example, the term "digital image" includes, but is not limited to, digital files with the following file extensions: JPG, TIFF, BMP, PNG, RAW, or PDF. Thus, a digital image includes digital data or a digital file for an image that is displayable via a graphical user interface of a display of a computing device.

The term "image capture device", similar terms, and terms representing structures with similar functions may include one or more of a digital camera, webcam, film camera, analog camera, digital video camera, scanner, facsimile machine, copy machine, infrared imager, (laser scanning) confocal reflectance microscope, confocal fluorescence microscope, optical coherence tomography (OCT), multiphoton fluorescence (MPF) microscope, second harmonic generation (SHG) microscope, fluorescence lifetime imaging microscope (FLIM), photo acoustic microscope or any other mechanism for acquiring an image of a subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image. A confocal endoscope that is compatible with the biopsy channel of a conventional endoscope can be used to capture images of epithelial cells in a method according to the invention.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming, and decision tree programming, may also be used to identify conditions. Alternatively, one or more digital filters may be passed through the image for locating specific conditions. These examples are provided for illustrative purposes with the understanding that any image processing technique may be used.

"Image segmentation" is the process of partitioning a digital image into multiple image segments, also known as image regions or image objects (sets of pixels). The goal of segmentation is to simplify and/or change the representation of an image into something that is more meaningful and easier to analyze. Image segmentation is typically used to locate objects and boundaries (lines, curves, etc.) in images. More precisely, image segmentation is the process of assigning a label to every pixel in an Image such that pixels with the same label share certain characteristics.

"Multi-task learning" occurs when multiple correlated tasks are performed and optimized simultaneously; learning occurs across all datasets at the same time to learn generalized representations of the data and constrain each task solution space to improve overall performance. A "network" is defined as one or more data links that enable the transport of electronic data between computer systems and/or modules and/or other electronic devices. As used herein, the term "neural network" refers to a machine learning model that is tuned (e.g., trained) based on inputs to approximate unknown functions. For instance, the term neural network includes one or more machine learning algorithms.

"Cell organization" as used herein means the components that make up the cell and how they are arranged inside it. "Epidermal tissue structure" as used herein includes keratinocytes at each distinct stage of differentiation; melanocytes; Langerhans cells; resident T lymphocytes and Merkel cells. "Epidermal tissue structure" includes cell organization, topology, geometry, arrangement, and architecture as these terms are defined herein. "Epidermal tissue structure" is a subset of "epithelial tissue structure."

"Epidermis" as used herein means the outer layer of skin, and is divided into five strata, which include the: stratum corneum, stratum lucidum, stratum granulosum, stratum spinosum, and stratum basale. The stratum corneum contains many layers of dead, anucleated keratinocytes that are essentially filled with keratin. The outermost layers of the stratum corneum are constantly shed, even in healthy skin. The stratum lucidum contains two to three layers of anucleated cells. The stratum granulosum contains two to four layers of cells that are held together by desmosomes that contain keratohyaline granules. The stratum spinosum contains eight to ten layers of modestly active dividing cells that are also held together by desmosomes. The stratum basale contains a single layer of columnar cells that actively divide by mitosis and provide the cells that are destined to migrate through the upper epidermal layers to the stratum corneum. The predominant cell type of the epidermis is the keratinocyte. These cells are formed in the basal layer and exist through the epidermal strata to the granular layer at which they transform into the cells know as corneocytes or squames that form the stratum corneum. During this transformation process, the nucleus is digested, the cytoplasm disappears, the lipids are released into the intercellular space, keratin intermediate filaments aggregate to form microfibrils, and the cell membrane is replaced by a cell envelope made of cross-linked protein with lipids covalently attached to its surface. Keratins are the major structural proteins of the stratum corneum. Corneocytes regularly slough off (a process known as desquamation) to complete an overall process that takes about a month in healthy human skin. In stratum corneum that is desquamating at its normal rate, corneocytes persist in the stratum corneum for approximately 2 weeks before being shed into the environment.

"Epithelial tissue structure" as used herein includes any of the cells making up an epithelium at each distinct stage of differentiation. "Epithelial tissue structure" includes cell organization, topology, geometry, arrangement, and architecture as these terms are defined herein. "Epithelium" as used herein means a thin, continuous, protective layer of cells that line the outer surfaces of organs and blood vessels throughout the body, as well as the inner surfaces of cavities in many internal organs. It is classified based on the number of layers that make up the tissue: simple, stratified, and pseudostratified. It may also be classified histologically, according to the cell shape: squamous, columnar, and cuboidal. It is primarily involved in providing protection of the underlying structures, secretory functions, transcellular transport, and selective absorption. Examples of epithelium include the epidermis; the lining of the digestive tract; and the lining of the reproductive tract.

A "skin condition" is anything that clogs, damages and/or irritates skin, and can includes, but is not limited to, acne, actinic keratosis, aging, alopecia areata, atopic dermatitis, basal cell carcinoma, cyst, eczema, folliculitis, hidradenitis, lentigo, melanocytic nevus, post inflammatory hyperpigmentation, psoriasis, squamous cell carcinoma or squamous cell carcinoma in situ, seborrheic keratosis, scar condition, seborrheic dermatitis, skin tag, stasis dermatitis, tinca, tinca *versicolor*, urticaria, verruca vulgaris, vitiligo, and other.

"Xavier initialization" is an attempt to improve the initialization of neural network weighted inputs, in order to avoid some traditional problems in machine learning. Here, the weights of the network are selected for certain intermediate values that have a benefit in machine learning application.

Embodiments of the present disclosure comprise or utilize a special purpose or general-purpose computer including computer hardware, such as, for example, one or more processors and system memory.

In the various embodiments described above, unless specifically noted otherwise, disjunctive language such as the phrase "at least one of A, B, or C," is intended to be understood to mean either A, B, or C, or any combination thereof (e.g., A, B, and/or C). As such, disjunctive language is not intended to, nor is it to be understood to, imply that a given embodiment requires at least one of A, at least one of B, or at least one of C to each be present.

7

Figure 1B:
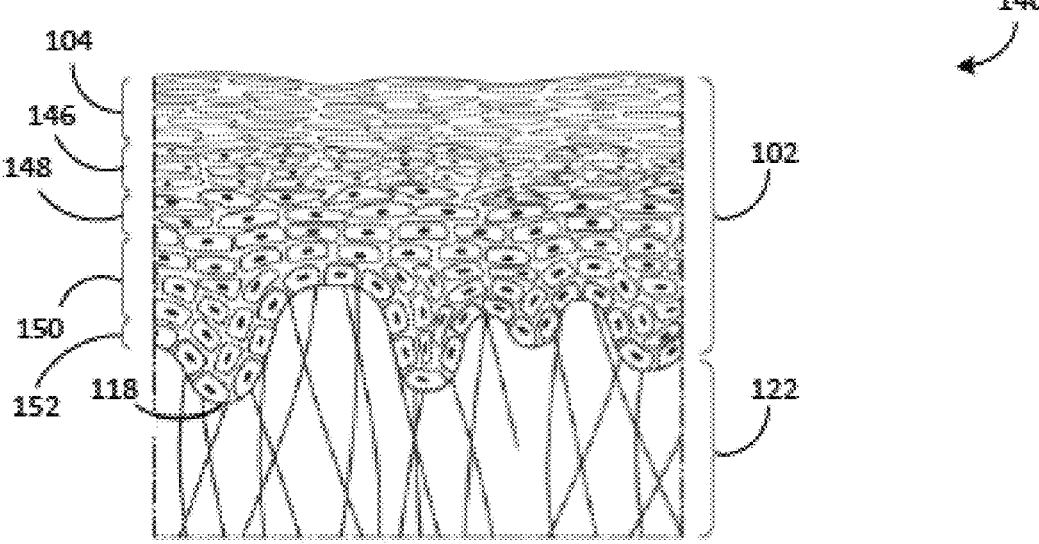

As described herein and illustrated in FIG. 1A, human skin 100 comprises three principal layers: the epidermis 102, the dermis 122, and the hypodermis 124, which is a layer of subcutaneous fat also. The epidermis 102 primarily comprises keratinocytes in progressive stages of differentiation. Keratinocytes produce the protein keratin and are the major building blocks (cells) of the epidermis. The epidermis 102 is avascular, meaning it contains no blood vessels, and is entirely dependent on the underlying dermis 122 for nutrient delivery and waste disposal through the dermis 122. FIG. 1B illustrates the various layers 140 of the skin, including the epidermis 142. The epidermis 102 is composed of the stratum corneum 104, also illustrated in FIG. 1A, the stratum lucidum 146, which is found in thick skin such as the palms of the hands, the soles of the feet and the digits, the stratum granulosum 148, the stratum spinosum 150, and the stratum basale 152.

Figure 2:
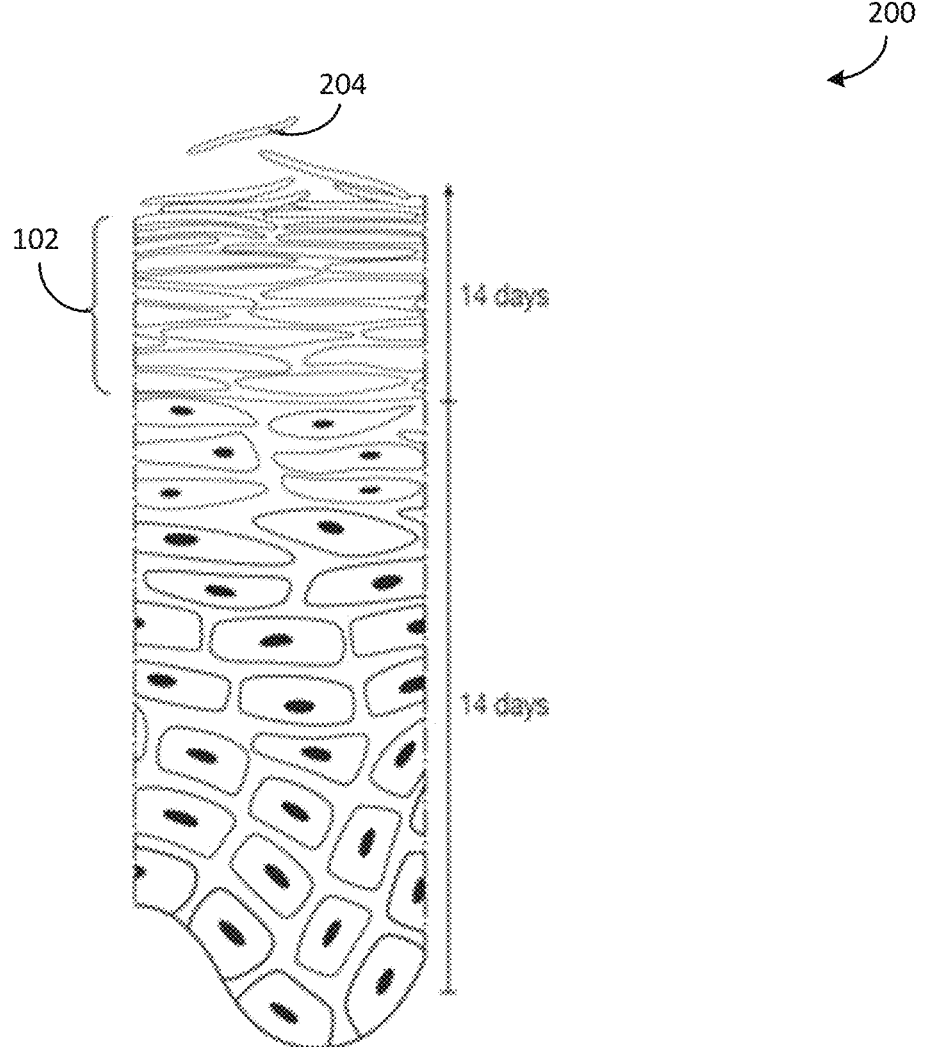
FIG. 2 illustrates the process of desquamation in human skin.

The epidermis 102 also contains other cell structures. Keratinocytes make up around 95% of the epidermal cell population, the remainder of which includes melanocytes 112, Langerhans cells, resident T lymphocytes and Merkel cells. Keratinocytes are formed by division in the stratum basale 152. As they move up through the stratum spinosum 150 and stratum granulosum 148, they differentiate through keratinization to form a rigid internal structure of keratin, microfilaments and microtubules. The outer layer of the epidermis 102, the stratum corneum 104, is composed of layers of flattened dead cells called corneocytes 204 that have lost their nucleus. These cells are then shed from the skin through desquamation. This complete process takes approximately 28 days and is illustrated in FIG. 2.

Between the corneocytes there is a complex mixture of intercellular lipids and proteins that are processed by enzymes from keratinocytes to produce a lipid mixture of ceramides (phospholipids), fatty acids, and cholesterol. These molecules are arranged in a highly organized fashion, fusing with each other and the corneocytes to form the skin's lipid barrier against water loss and penetration by allergens and irritants. Corneocytes contain water-retaining substances, collectively referred to as natural moisturizing factors, that attract and hold onto water. The water content of the corneocytes controls their pliability and elasticity, preventing the formation of fissures and cracks. The highly organized structure of the stratum corneum regulates the amount and rate of percutaneous absorption. One of the most important factors affecting this is skin hydration and environmental humidity.

Melanocytes 112 are found in the stratum basale 152 and are scattered among the keratinocytes along the basement membrane 118. Melanocytes 112 produce the pigment melanin, manufactured from tyrosine, which is an amino acid, packaged into cellular vesicles called melanosomes, and transported and delivered into the cytoplasm of the keratinocytes. The main function of melanin is to absorb ultraviolet (UV) radiation to protect against its harmful effects. The pattern of epithelial tissue structure organization is important in distinguishing between diseased/damaged and normal skin. Thus, epithelial tissue structure organization may be a target for therapeutic and cosmetic skin products.

The dermis 122 includes fibroblasts and an extracellular matrix composed mainly of collagen and elastin. The dermis 122 includes sweat glands 106 that excrete sweat 108 on the surface of the epidermis 102, capillaries 110 that provide blood flow through the dermis 122 from blood vessels 128a, 128b in the hypodermis 124, hair 114 extending through the epidermis 102 from a hair follicle 126, a sebaceus gland 120, and a basement membrane 118 between the dermis 122 and the epidermis 102. The hypodermis 124 includes the blood vessels 128a, 128b and a nerve 130 that extends through the hypodermis 124, the dermis 122, and the epidermis 102.

The present disclosure provides a technical effect of reducing consumption of computing resources for training and operating cycle-GANs and ultimately analyzing images generated by the cycle-GANs. For example, the cycle-GAN models provided in the present disclosure not only have the specificity of training two pairs of generator/discriminator models for unpaired image-to-image translation simultaneously, but also introduce a cycle-consistency loss to train both pairs simultaneously. By using a cycle-consistency loss to train both pairs simultaneously, the data requirement is eliminated as there is no requirement for dual image acquisition of a single sample, which often is not possible due to the destructive nature of other methods. Thus, the present disclosure proposes to use two cycle GAN models in a multi-task learning approach that performs multiple related, but not identical, tasks in parallel and leverages information from all of them to improve the overall performance.

The present disclosure further provides a technical solution to the technical problem of analysis of epidermal cells on RCM images. Accurate segmentation of epidermal cells on RCM images is important in the study of epidermal architecture and topology of both healthy and diseased skin. However, analysis of these images, which is currently done manually, is time-consuming, subject to human error and inter-expert interpretation, and hindered by low image quality due to noise and heterogeneity. To address these this technical challenge, the present disclosure provides a technical solution of a dual-task network that automatically segments RCM images, an image generator that generates an image based on the automatically segmented RCM images, and an image analyzer that performs an analysis on the generated image. Each task in the dual-task network includes a cycle Generative Adversarial Network (GAN). The first task translates real RCM images into synthetic segmentations, and thus learning the noise model of RCM images, while the second task maps Gabor-filtered real RCM images into binary segmentations, and thus learning the structure of RCM images. The combination of the two tasks teaches the model structure, with one task constricting the solution space of the other and improving overall results. Segmentation is refined by applying an algorithm, such as the StarDist algorithm, to detect star-convex shapes, thus closing any incomplete membranes and separating neighboring cells. As referenced herein, StarDist is a deep-learning-based method of two-dimensional (2D) and three-dimensional (3D) nucleus detection that successfully segments RCM images of the epidermis with an accuracy on par with experts' segmentation. Table 1 below illustrates accuracy measures on 9 reflectance confocal microscopy images.

TABLE 1

| | MTCGANs | | |
|---|---|---|---|
| Images | Precision | Recall | F1-score |
| 1 | 0.684 | 0.736 | 0.709 |
| 2 | 0.779 | 0.510 | 0.616 |
| 3 | 0.725 | 0.607 | 0.661 |
| 4 | 0.649 | 0.820 | 0.725 |
| 5 | 0.534 | 0.851 | 0.656 |
| 6 | 0.532 | 0.848 | 0.654 |
| 7 | 0.639 | 0.920 | 0.754 |
| 8 | 0.658 | 0.758 | 0.704 |

TABLE 1-continued

| | MTCGANs | | |
|---|---|---|---|
| Images | Precision | Recall | F1-score |
| 9 | 0.574 | 0.866 | 0.690 |
| MEDIAN | 0.649 | 0.820 | 0.690 |
| STD | 0.084 | 0.133 | 0.042 |

Figure 3:
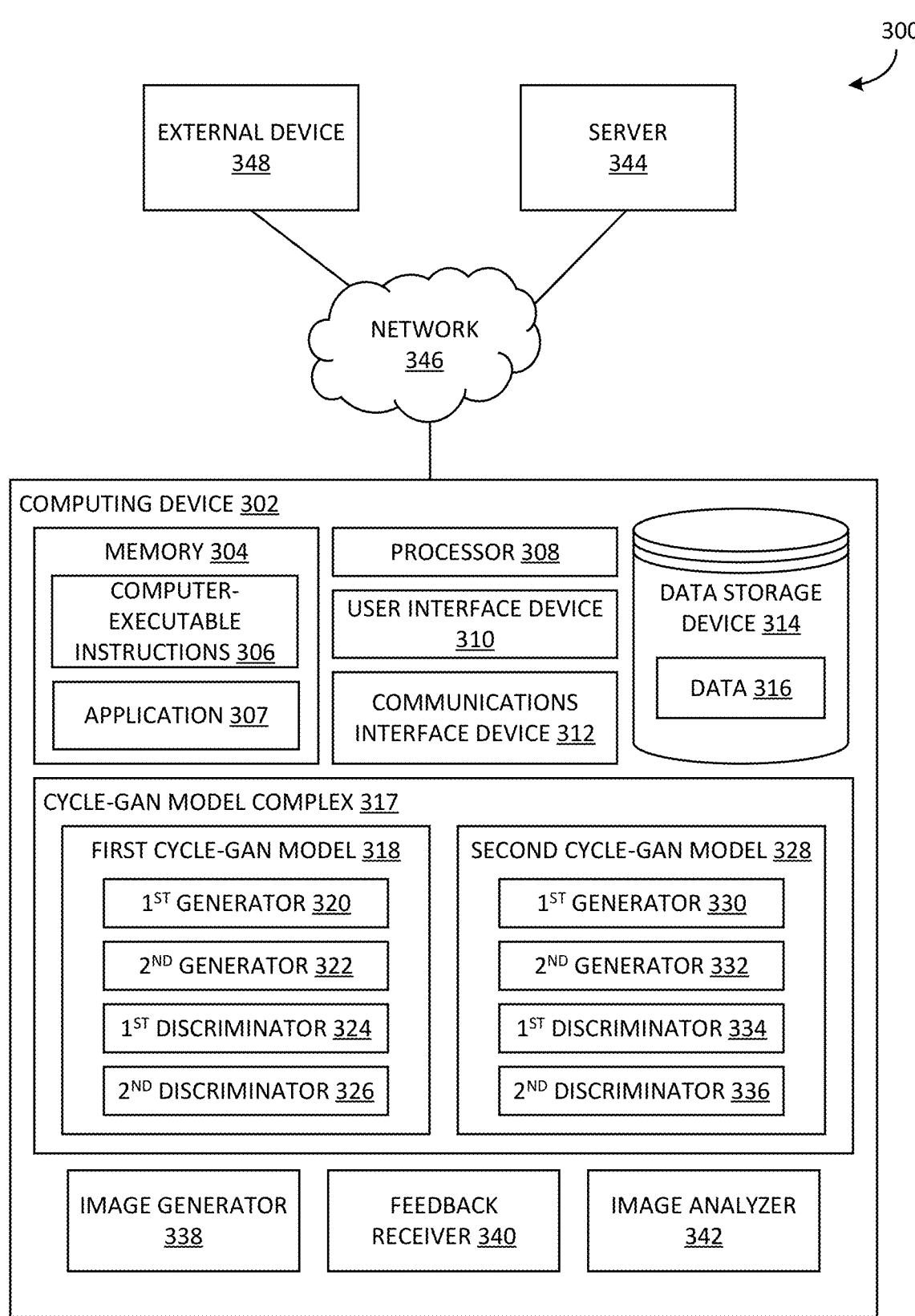
FIG. 3 illustrates an example system for performing cell identification.

For example, FIG. 3 illustrates an example system for performing cell identification. The system 300 illustrated in FIG. 3 is provided for illustration only. Other examples of the system 300 can be used without departing from the scope of the present disclosure.

The system 300 includes a computing device 302, an external device 348, a server 344, and a network 346. The computing device 302 represents any device executing computer-executable instructions 306 (e.g., as application programs, operating system functionality, or both) to implement the operations and functionality associated with the computing device 302. The computing device 302 in some examples includes a mobile computing device or any other portable device. A mobile computing device includes, for example but without limitation, a mobile telephone, laptop, tablet, computing pad, netbook, gaming device, and/or portable media player. The computing device 302 can also include less-portable devices such as servers, desktop personal computers, kiosks, or tabletop devices. Additionally, the computing device 302 can represent a group of processing units or other computing devices.

In some examples, the computing device 302 includes at least one processor 308, a memory 304 that includes the computer-executable instructions 306, and a user interface device 310. The processor 308 includes any quantity of processing units and is programmed to execute the computer-executable instructions 306. The computer-executable instructions 306 are performed by the processor 308, performed by multiple processors within the computing device 302, or performed by a processor external to the computing device 302. In some examples, the processor 308 is programmed to execute computer-executable instructions 306 such as those illustrated in the figures described herein, such as FIGS. 5, 7, and 8. In various examples, the processor 308 is configured to execute computer-executable instructions of the cycle-GAN model complex 317, the image generator 338, the feedback receiver 340, and the image analyzer 342 as described herein.

The memory 304 includes any quantity of media associated with or accessible by the computing device 302. In some examples, the memory 304 is internal to the computing device 302. In other examples, the memory 304 is external to the computing device 302 or both internal and external to the computing device 302. For example, the memory 304 can include both a memory component internal to the computing device 302 and a memory component external to the computing device 302, such as the server 344. The memory 304 stores data, such as one or more applications 307. The applications 307, when executed by the processor 108, operate to perform various functions on the computing device 302. The applications 307 can communicate with counterpart applications or services, such as web services accessible via the network 346. In an example, the applications 307 represent server-side services of an application executing in a cloud, such as a cloud server 344.

The user interface device 310 includes a graphics card for displaying data to a user and receiving data from the user. The user interface device 310 can also include computer-executable instructions, for example a driver, for operating the graphics card. Further, the user interface device 310 can include a display, for example a touch screen display or natural user interface, and/or computer-executable instructions, for example a driver, for operating the display. The user interface device 310 can also include one or more of the following to provide data to the user or receive data from the user: speakers, a sound card, a camera, a microphone, a vibration motor, one or more accelerometers, a BLUETOOTH® communication module, global positioning system (GPS) hardware, and a photoreceptive light sensor. In a non-limiting example, the user inputs commands or manipulates data by moving the computing device 302 in one or more ways.

The computing device 302 further includes a communications interface device 312. The communications interface device 312 includes a network interface card and/or computer-executable instructions, such as a driver, for operating the network interface card. Communication between the computing device 302 and other devices, such as but not limited to the external device 348, can occur using any protocol or mechanism over any wired or wireless connection.

The computing device 302 further includes a data storage device 314 for storing data 316. The data 316 includes, but is not limited to, a database storing information reflecting relationships between categories of user-specific information and skin care treatment information, including relationships derived from known epidermal tissue structure model image segment for skin care treatment obtained using artificial intelligence. For example, a category of user-specific information may include skin history, such as acne, eczema, injury, previous treatment history, familial history if provided by the user, and so forth. Skin care treatment information may include one or more of a skin care treatment, regimen, ingredient, formula, product, and so forth.

The data storage device 314 can include one or more different types of data storage devices, such as, for example, one or more rotating disks drives, one or more solid state drives (SSDs), and/or any other type of data storage device. The data storage device 314 in some non-limiting examples includes a redundant array of independent disks (RAID) array. In other examples, the data storage device 314 includes a database. The data storage device 314, in this example, is included within the computing device 302, attached to the computing device 302, plugged into the computing device 302, or otherwise associated with the computing device 302. In other examples, the data storage device 314 includes a remote data storage accessed by the computing device 302 via the network 346, such as the server 344, which may be a remote data storage device, a data storage in a remote data center, a cloud storage, and so forth.

The computing device 302 further includes a cycle-GAN model complex 317. The cycle-GAN model complex 317 includes a first cycle generative adversarial network (cycle-GAN) model 318 and a second cycle-GAN model 328. A cycle-GAN is a machine learning model in which the aim is to learn the translation from one dataset to another when the datasets are unrelated. In some examples, each of the first cycle-GAN model 318 and the second cycle-GAN model 328 execute in parallel, i.e., execute their respective tasks simultaneously. In other examples, the first cycle-GAN model 318 and the second cycle-GAN model 328 operate at different times, i.e., the first cycle-GAN model 318 operates at a first time and the second cycle-GAN model 328 operates at a second time. For example, the tasks performed by the second cycle-GAN model 328 may depend on an output of the first cycle-GAN model 318, or vice versa.

Each of the first cycle-GAN model 318 and the second cycle-GAN model 328 is made of four networks: two generators and two discriminators. For example, the first cycle-GAN model 318 includes a first generator 320, a second generator 322, a first discriminator 324, and a second discriminator 326. Similarly, the second cycle-GAN model 328 includes a first generator 330, a second generator 332, a first discriminator 334, and a second discriminator 336. In some examples, the first generator 320 is referenced as GB2A, the second generator 322 is referenced as GA2B, the first discriminator 324 is referenced as DA, the second discriminator 326 referenced as DB1, the first generator 330 is referenced as GC2B, the second generator 332 is referenced as GB2C, the first discriminator 334 is referenced as DC, and the second discriminator 336 is referenced as DB2.

Each generator in a cycle-GAN is a convolutional neural network and each discriminator in a cycle-GAN is a deconvolutional neural network. The goal of the generator is to artificially manufacture, using images from a first dataset, outputs that could easily be mistaken for images from the second dataset, while the goal of the discriminator is to identify which outputs it receives have been artificially created. This creates a feedback loop between the generator and discriminator that, as it continues, enables the generator to produce higher-quality outputs and the discriminator to become better at flagging data that has been artificially created. In some examples, a cycle-GAN is used to improve an original image in some way. For example, a cycle-GAN may demonstrate photo enhancement by improving the depth of the field.

A cycle-GAN operates by identifying a desired end output and gathering two initial training datasets based on those parameters. This data is then randomized and input into each generator until it acquires basic accuracy in producing outputs. The generated images are then fed into the discriminator along with actual data points from the original concept. The discriminator filters through the information and returns a probability between 0 and 1 to represent each image's authenticity (1 correlates with real and 0 correlates with fake). These values are then manually checked for success and repeated until the desired outcome is reached. In some examples, cycle-GAN are used in performing multi-task learning (MTL). MLT is a subfield of machine learning in which multiple tasks are simultaneously learned by a shared model using shared representations to learn the common ideas between a collection of related tasks.

For example, the first cycle-GAN model 318 and the second cycle-GAN model 328 may execute and tasks simultaneously. More specifically, the first cycle-GAN model 318 includes the first generator 320 and the first discriminator 324 that together perform a first task, and the second generator 322 and the second discriminator 326 that together perform a second task, while the second cycle-GAN model 328 includes the first generator 330 and the first discriminator 334 that together perform a first task, and the second generator 332 and the second discriminator 336 that together perform a second task.

Executing the first cycle-GAN model 318 and the second cycle-GAN model 328 simultaneously addresses current challenges with training models to generate images of cell tissue, as current models fail to either accurately identify and remove noise from complex images, accurately identify tissue structures in complex images, or both. By simultaneously implementing the first cycle-GAN model 318 and the second cycle-GAN model 328, the models provided in the present disclosure are enabled to remove noise from real images while maintaining the position and integrity of structural membranes to generate a new, improved image. The improved image may then be used to characterize one or more epithelial tissue structures in the image, such as identifying cell coordinates information that is used to extract values of epithelial tissue structure parameters. In some examples, the real images are acquired by non-invasive or minimally invasive imaging with cellular resolution. In various examples, the non-invasive or minimally invasive imaging is selected from the group consisting of reflectance confocal microscopy (RCM), fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy.

The first cycle-GAN model 318 removes noise from an input set of images. For example, the first generator 320 receives, as an input, a real image and generates, as an output, a synthetic image. The received real image may be an RCM image captured by an external device, such as the external device 348, and transmitted to the computing device 302 and received via the communications interface device 312. In another example, the received real image may be captured by the computing device 302 itself. The first discriminator 324 receives each of the real image and the generated synthetic image from the first generator 320 and generates a determination that includes a prediction of whether each image is real or synthetic. Thus, the prediction generated by the first discriminator 324 may be correct, by correctly predicting which image is real and which image is synthetic, or incorrect, by incorrectly predicting which image is real and which image is synthetic.

The second generator 322 receives, as an input, the real image and the generated synthetic image and generates, as an output, a filtered synthetic image. The second discriminator 326 receives each of the real image and the filtered synthetic image and generates a determination that includes a prediction of whether each image is real or generated by the model. Thus, the prediction generated by the second discriminator 326 may be correct, by correctly predicting which image is real and which image is generated, or incorrect, by incorrectly predicting which image is real and which image is generated. Accordingly, the first cycle-GAN model 318 is continuously trained to learn to identify and remove noise from a real image by learning the translation from an input real image toward binary segmentation.

The second cycle-GAN model 328 learns image structure of cellular tissue once the noise has been removed from the input image by the first cycle-GAN model 318. For example, the first generator 330 receives, as an input, filtered images and generates, as an output, a synthetic image. In some examples, the received filtered images are Gabor-filtered images. As referenced herein, a Gabor filter is a linear filter used for texture analysis that analyzes whether there is any specific frequency content in the image in specific directions in a localized region around the point or region of analysis. The filtered images may be filtered by the processor 308, such as by executing an application 307 stored on the memory 304 or may be received as pre-filtered images from an external device 348. The first discriminator 334 receives each of the filtered image and the generated synthetic image from the first generator 330 and generates a determination that includes a prediction of whether each image is filtered or generated by the model. Thus, the prediction generated by the first discriminator 334 may be correct, by correctly predicting which image is filtered and which image is generated, or incorrect, by incorrectly predicting which image is filtered and which image is generated.

The second generator 332 receives, as an input, the filtered image and the generated synthetic image and generates, as an output, a filtered synthetic image. The second discriminator 336 receives each of the filtered image and the synthetic image and generates a determination that includes a prediction of whether image is filtered or synthetic. Thus, the prediction generated by the second discriminator 323 may be correct, by correctly predicting which image is filtered and which image is the filtered synthetic image, or incorrect, by incorrectly predicting which image is filtered and which image is the filtered synthetic image. Accordingly, the second cycle-GAN model 328 is continuously trained to learn structure of tissue and cells within epithelial tissues by learning the translation from the filtered images toward binary segmentation.

Thus, the present disclosure therefore provides an image denoiser, i.e., the first cycle-GAN model 318, and a cell segmenter, i.e., the second cycle-GAN model 328, that learns local and global texture of the image. By simultaneously training two cycle-GANs, one which learns the noise through learning the translation from real images towards binary segmentations, and one which learns structure through learning the translation from Gabor-filtered images towards binary segmentation, the structure of tissue and cells within epithelial tissues is more effectively learned. It should be understood that as described herein, the first cycle-GAN model 318 and the second cycle-GAN model 328 are connected through soft-sharing of parameters as they do not share any hidden layer but are combined through their loss function.

The computing device 302 further includes an image generator 338. The image generator 338 is an example of a specialized processing unit, implemented on the processor 308, that implements the trained cycle-GAN model complex 317, including the first cycle-GAN model 318 and the second cycle-GAN model 328, to generate an improved epithelial tissue structure image. In some examples, the image generated by the image generator 338 is referred to herein as an artificially generated image. The improved epithelial tissue structure image is improved over existing synthetic images due to the improved learning of epithelial tissue structure due to the implementation of the second cycle-GAN model 328, which in turn is improved due to the implementation of the first cycle-GAN model 318 that learns to reduce noise in the tissue structure image.

The computing device 302 further includes a feedback receiver 340. The feedback receiver 340 receives feedback, such as via the user interface device 310 or the communication interface device 312 from an external device 348, regarding the artificially generated images generated by the image generator 338. Feedback received via the feedback receiver 340 is used to continuously train the first cycle-GAN model 318 and the second cycle-GAN model 328 to improve the noise identification and structure identification aspects, respectively, in order for the image generator 338 to continuously generate improved artificially generated images.

The computing device 302 further includes an image analyzer 342. The image analyzer 342 is a specialized processing unit implemented on the processor 308 that analyzes the artificially generated image or images generated by the image generator 338. In some examples, the image analyzer 342 executes an algorithm to identify cell coordinates information that is used to extract values of epithelial tissue structure parameters. The epithelial cell coordinates information may be employed to extract values of cell geometry and cell topology parameters. In some examples, the parameters are selected from cell area, perimeter, cell density, distribution of nearest neighbors, and distributions of distances between neighbors. In some examples, the image analyzer 342 uses the parameters to compare images for screening for appropriate treatment selected from use of ingredients and use of formulations.

In some examples, the image analyzer 342 is implemented to characterize a training set of epithelial tissue structure improved images to be used for screening for appropriate treatment selected from use of ingredients and use of formulations.

In some examples, the image analyzer 342 is implemented to screen a skin treatment regimen, ingredient, or composition for a benefit to skin by analyzing the artificially generated image generated by the image generator 338. For example, the image analyzer 342 may first compare an unknown image segment to an improved epithelial tissue structure image generated by the image generator 338 to determine the degree of match between the unknown segment and the improved epithelial tissue structure image prior to application of the skin treatment regimen, ingredient, or composition and then, following an application of the skin treatment regimen, ingredient, or composition to the area of skin for a period of time, compare an unknown image segment to the previous improved epithelial tissue structure image to determine the degree of match between the unknown segment and the improved epithelial tissue structure image after the skin treatment regimen, ingredient, or composition application. The image analyzer 342 may determine the skin treatment regimen, ingredient, or composition is of benefit to skin if within a confidence level, e.g., greater than 90% of the level of the degree of match between the unknown segment and the improved epithelial tissue structure image changes vs. the no treatment control.

In this example, the regimen, ingredient, or composition may have an application time on the skin. For example, the application time may be between about 1 minute to about 4 weeks. For example, the application time may be between five minutes and twenty-four hours, at least seven days, at least twenty-one days, or any other suitable time frame depending on the regimen, ingredient, or composition. In some examples, the skin treatment regimen, ingredient, or composition enhances one or more attributes selected from the group consisting of reduction of visual dryness, reduction of trans-epidermal water loss, and increase in skin hydration.

In some examples, the image analyzer 342 is implemented to provide an aspect of a skin care treatment. For example, the image analyzer 342 may receive user-specific information that includes an unknown image segment of interest, such as a segment of interest from an artificially generated image generated by the image generator 338 and compare the received image to a known epidermal tissue structure image to determine a degree of match. The image analyzer 342 may then access a data structure, such as the data storage device 314 or an external storage location such as the server 344, containing data 316 that includes information reflecting relationships between categories of user-specific information and skin care treatment information, including relationships derived from known epidermal tissue structure model image segment for skin care treatment obtained using artificial intelligence. The image analyzer 342 compares the received user-specific information with the accessed data 316 and identifies a skin care treatment recommendation determined by the artificial intelligence engine to be related to the user-specific information. The identified skin care treatment is provided to the user, such as by presenting the identified skin care treatment on the user interface device 310 or transmitting, via the communications interface device 312, to the external device 348.

In some examples, as shown in FIG. 3, the image analyzer 342 is implemented on the computing device 302. However, various examples are possible without departing from the scope of the present disclosure. For example, the image analyzer 342 may be implemented on an external device, such as the external device 348, and results of the analysis by the image analyzer 342 may be transmitted to the computing device 302 via the network 346 and received at the computing device 302 by the communications interface device 312.

Figure 4:
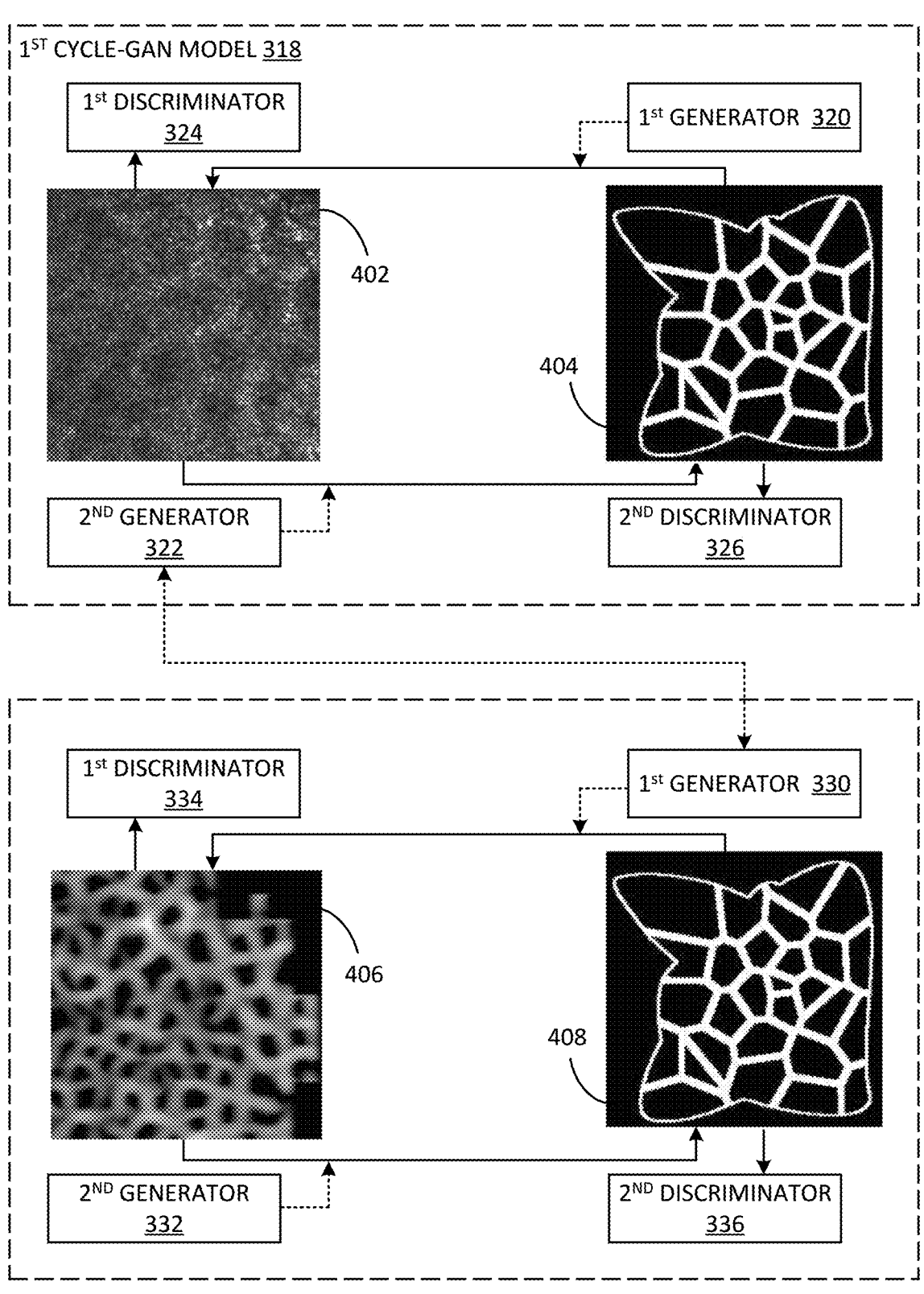
FIG. 4 illustrates an example architecture for training pairs of cycle-GAN models simultaneously.

FIG. 4 illustrates an example architecture for training pairs of cycle-GAN models simultaneously according to various examples of the present disclosure. The architecture 400 illustrated in FIG. 4 is provided for illustration only. Other examples of the architecture 400 can be used without departing from the scope of the present disclosure.

The architecture 400 includes the first cycle-GAN model 318 and the second cycle-GAN model 328. The first cycle-GAN model 318 receives, as a first input, a first real image 402. Through the process described herein, the first generator 320 receives the first real image 402 and generates a first synthetic image which is received by the first discriminator 324. The first discriminator 324 informs a likelihood of each of the first real image 402 and the first synthetic image being real or synthetic. The second generator 322 receives the first real image 402 and first synthetic image and generates a filtered synthetic image 404. The second discriminator 326 informs a likelihood of each of the first real image 402 and the filtered synthetic image 404 as being real or synthetic, i.e., generated by the model. The first cycle-GAN model 318 estimates a mapping GA2B from the RCM image domain A toward a binary domain B. Thus, the first cycle-GAN model 318 is trained to learn noise through learning a translation from the first real image 402 towards binary synthetic segmentations.

The second cycle-GAN model 328 receives, as a second input, a filtered image 406, such as a Gabor-filtered image and generates a second synthetic image as a second output which is received by the first discriminator 334. The first discriminator 334 informs a likelihood of each of the filtered image 406 and the second synthetic image as being filtered or generated by the model. The second generator 332 receives the filtered image 406 and the second synthetic image and generates a filtered synthetic image 408. The second discriminator 336 informs a likelihood each of the filtered image 406 and the filtered synthetic image 408 as being real or generated by the model. The second cycle-GAN model 328 is trained to map filtered RCM images, in domain C where membranes have been highlighted and noise has been removed, into binary, i.e., synthetic, images. Thus, the second cycle-GAN model 328 is trained to learn a structure, such as parameters, through learning a translation from the Gabor-filtered image towards binary segmentation. For example, the structure may be a global geometrical structure of epidermal cell populations or other cell populations.

It should be understood that as the first cycle-GAN model 318 and the second cycle-GAN model 328 are trained simultaneously in tandem, the first cycle-GAN model 318 and the second cycle-GAN model 328 are trained using a cycle-consistency loss. Using the cycle-consistency loss to train the first cycle-GAN model 318 and the second cycle-GAN model 328 are reduces the data requirement for the training, as there is no requirement for dual image acquisition of a single sample. Oftentimes, the dual image acquisition is not possible due to the destructive nature of certain methods. Thus, the present disclosure provides a technical solution that utilizes two cycle-GAN models with a cycle-consistency loss that reduces data requirements in a multi-task learning approach by performing multiple related, but not identical tasks, in parallel. This leverages information from both cycle-GAN models to improve the overall performance of the cycle-GAN model complex 317.

Figure 5:
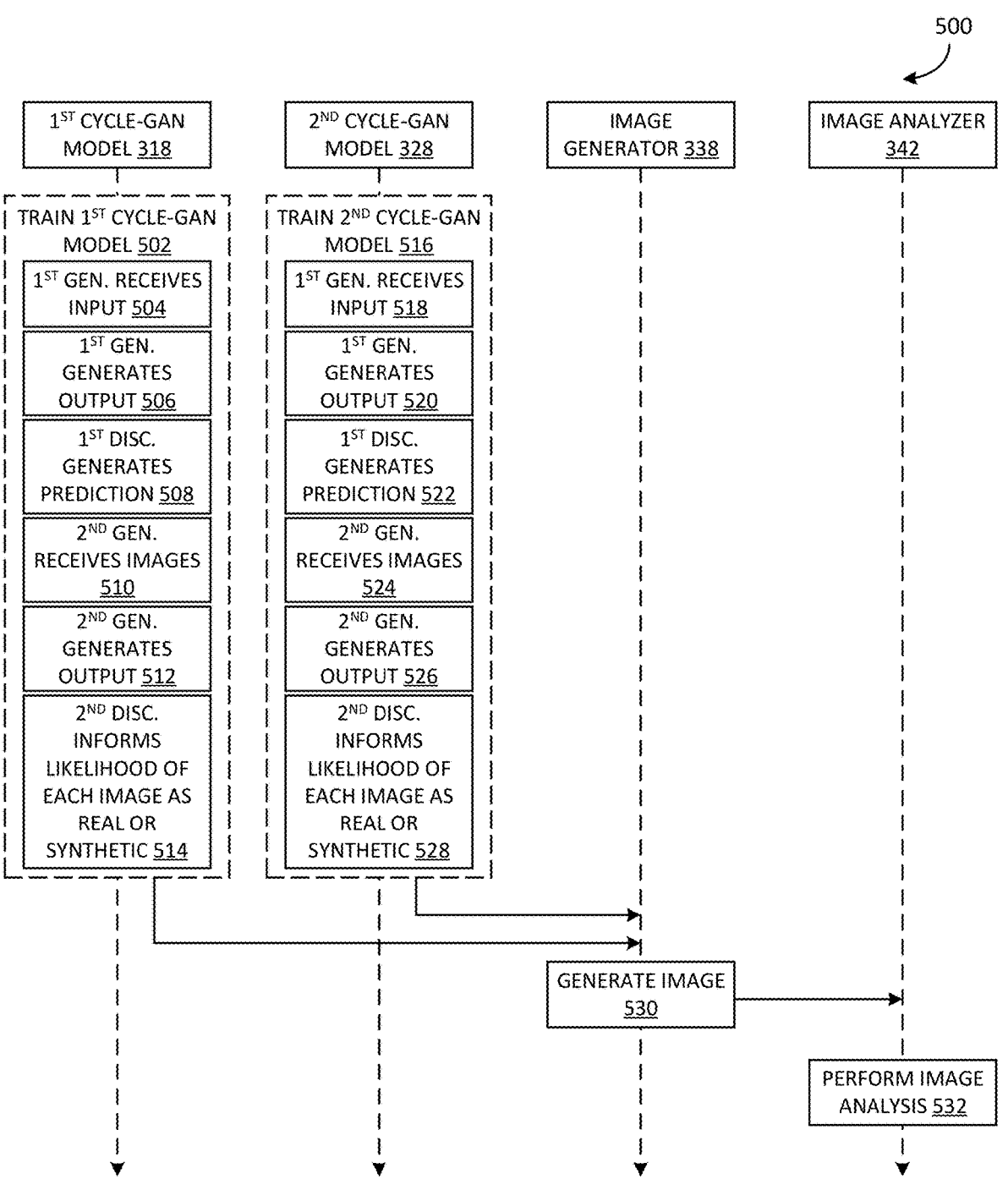
FIG. 5 illustrates an example computer-implemented method of training pairs of cycle-GAN models simultaneously.

FIG. 5 illustrates an example computer-implemented method of training pairs of cycle-GAN models simultaneously. The computer-implemented method 500 is presented for illustration only and should not be construed as limiting. Other examples of the computer-implemented method 500 can be used without departing from the scope of the present disclosure. The computer-implemented method 500 can be implemented by one or more electronic devices described herein, such as the computing device 302.

As illustrated in FIG. 5, a first cycle-GAN model, such as the first cycle-GAN model 318, and a second cycle-GAN model, such as the second cycle-GAN model 328, are trained simultaneously using cycle-consistency loss. For example, in operation 502 the first cycle-GAN model 318 is trained and in operation 516, the second cycle-GAN model 328 is trained. However, in some examples one cycle-GAN model may be trained before the other cycle-GAN model is trained, or training for one cycle-GAN model may begin prior to the training of another cycle-GAN model.

The training of the first cycle-GAN model 318 in operation 502 includes a plurality of steps. In operation 504, the first generator 320 receives a first real image as an input. In some examples, the received real image is an RCM image captured by an external device, such as the external device 348, and transmitted to the computing device 302 and received via the communications interface device 312. In another example, the received real image is captured by the computing device 302 itself. In operation 506, the first generator 320 generates an output based on the received first real image. In some examples, the generated output is, or includes a synthetic image.

In operation 508, the first discriminator 324 receives the real image and the generated synthetic image from the first generator 320 and generates a determination that includes a prediction of whether each image is real or synthetic. Accordingly, the prediction generated by the first discriminator 324 may be correct, by correctly predicting which image is real and which image is synthetic, or incorrect, by incorrectly predicting which image is real and which image is synthetic. In operation 510, the second generator 322 receives, as an input, the real image and the synthetic image. In operation 512, the second generator 322 generates, as an output, a filtered synthetic image. In operation 514, the second discriminator 326 receives each of the real image and the filtered synthetic image from the second generator 322 and generates a determination that includes a prediction of whether each image is real or synthetic. Accordingly, the prediction generated by the second discriminator 326 may be correct, by correctly predicting which image is real and which image is synthetic, or incorrect, by incorrectly predicting which image is real and which image is synthetic. Thus, the first cycle-GAN model 318 is continuously trained in operation 502 to learn to identify and remove noise from a real image by learning the translation from an input real image toward binary segmentation.

Simultaneously, i.e., as operation 502 occurs, the second cycle-GAN model 328 is trained in operation 516 to learn image structure of cellular tissue once the noise has been removed from the input image by the first cycle-GAN model 318. The training of the second cycle-GAN model 328 in operation 516 includes a plurality of steps. In operation 518, the first generator 330 receives, as an input, filtered images. In some examples, the received filtered images are Gabor-filtered images. The filtered images may be filtered by the processor 308, such as by executing an application 307 stored on the memory 304 or may be received as pre-filtered images from an external device 348. In operation 520, the first generator 330 generates an output that is, or includes, a synthetic image.

In operation 522, the first discriminator 334 receives each of the filtered image and the generated synthetic image from the first generator 330 and generates a prediction of whether each image is filtered or synthetic. Accordingly, the prediction generated by the first discriminator 334 may be correct, by correctly predicting which image is filtered and which image is synthetic, or incorrect, by incorrectly predicting which image is filtered and which image is synthetic. In operation 524, the second generator 332 receives, as an input, the filtered image and the generated synthetic image. In operation 526, the second generator 332 generates, as an output, a filtered synthetic image. In operation 528, the second discriminator 336 receives each of the filtered image and the filtered synthetic image and generates a determination that includes a prediction of whether image is a filtered image or a filtered synthetic image. Accordingly, the prediction generated by the second discriminator 323 may be correct, by correctly predicting which image is filtered and which image is a filtered synthetic image, or incorrect, by incorrectly predicting which image is filtered and which image is a filtered synthetic image. Thus, the second cycle-GAN model 328 is continuously trained in operation 516 to learn to identify structure of tissue and cells within epithelial tissues by learning the translation from the filtered images toward binary segmentation.

In operation 530, the image generator 338 generates an improved epithelial tissue structure image, also referred to as an artificially generated image. The improved epithelial tissue structure image is improved over existing synthetic images due to the improved learning of epithelial tissue structure due to the implementation of the second cycle-GAN model 328, which in turn is improved due to the implementation of the first cycle-GAN model 318 that learns to reduce noise in the tissue structure image.

In operation 532, the image analyzer 342 performs an image analysis on the artificially generated image. Depending on a type of application of the image analyzer 342, various examples of image analysis are possible. In some examples, the image analyzer 342 executes an algorithm to identify cell coordinates information that is used to extract values of epithelial tissue structure parameters. The epithelial cell coordinates information may be employed to extract values of cell geometry and cell topology parameters. In some examples, the image analyzer 342 is implemented to characterize a training set of epithelial tissue structure improved images to be used for screening for appropriate treatment selected from use of ingredients and use of formulations. In some examples, the image analyzer 342 is implemented to screen a skin treatment regimen, ingredient, or composition for a benefit to skin. For example, the image analyzer 342 may first compare an unknown image segment to an improved epithelial tissue structure image generated by the image generator 338 to determine the degree of match between the unknown segment and the improved epithelial tissue structure image prior to application of the skin treatment regimen, ingredient, or composition and then, following an application of the skin treatment regimen, ingredient, or composition to the area of skin for a period of time, compare an unknown image segment to the previous improved epithelial tissue structure image to determine the degree of match between the unknown segment and the improved epithelial tissue structure image after the skin treatment regimen, ingredient, or composition application.

In some examples, the image analyzer 342 is implemented to provide an aspect of a skin care treatment. For example, the image analyzer 342 may receive user-specific information that includes an unknown image segment of interest, such as a segment of interest from an artificially generated image generated by the image generator 338 and compare the received image to a known epidermal tissue structure image to determine a degree of match. The image analyzer 342 may then access a data structure, such as the data storage device 314 or an external storage location such as the server 344, containing data 316 that includes information reflecting relationships between categories of user-specific information and skin care treatment information, including relationships derived from known epidermal tissue structure model image segment for skin care treatment obtained using artificial intelligence. The image analyzer 342 compares the received user-specific information with the accessed data 316 and identifies a skin care treatment recommendation determined by the artificial intelligence engine to be related to the user-specific information.

Figures 6A, 6B, 6C:
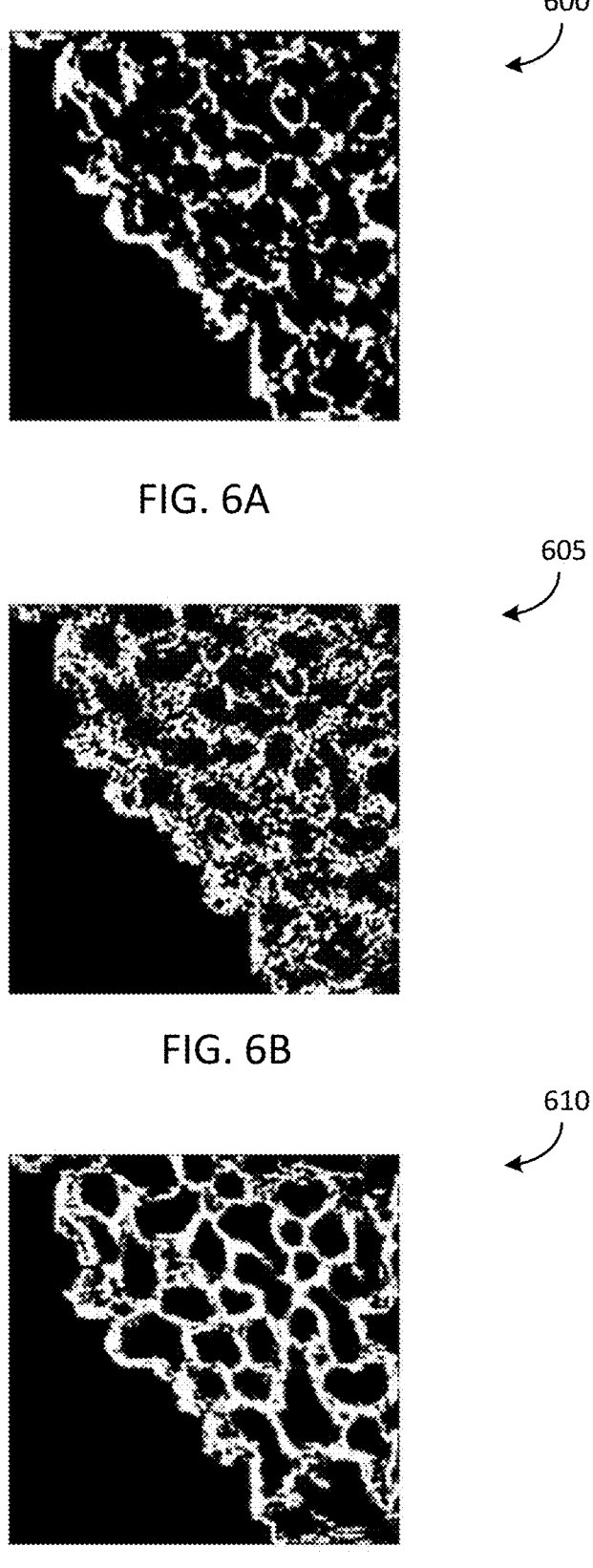
FIG. 6A illustrates an example image generated by a single task cycle-GAN model using an RCM image.
FIG. 6B illustrates an example image generated by a single task cycle-GAN model using a Gabor-filtered image.
FIG. 6C illustrates an example image generated by a multi-task cycle-GAN model.

FIG. 6A illustrates an example image 600 generated by a single task cycle-GAN model using an RCM image. FIG. 6B illustrates an example image 605 generated by a single task cycle-GAN model using a Gabor-filtered image. FIG. 6C illustrates an example image 610 generated by a multi-task cycle-GAN model. The example images illustrated in FIGS. 6A-6C are for illustration only and should not be construed as limiting. Other examples of the images are possible without departing from the scope of the present disclosure.

Each of the images illustrated in FIGS. 6A-6C illustrate different resulting images generated by different types of cycle-GAN models from the same real image. As illustrated in FIGS. 6A-6C, the multi-task cycle-GAN model, such as the multi-task cycle-GAN model complex 317, generates the image having the most accurate and precise parameters, such as cell boundaries, when compared to the images in FIGS. 6A and 6B. For example, the example image 600 is generated without being trained to identity cell boundaries from the original image while the example image 605 is generated without being trained to remove noise from the original image. In contrast, the example image 610 is generated after being trained to remove noise from the original image as well as identify cell boundaries from the original image.

Figure 7:
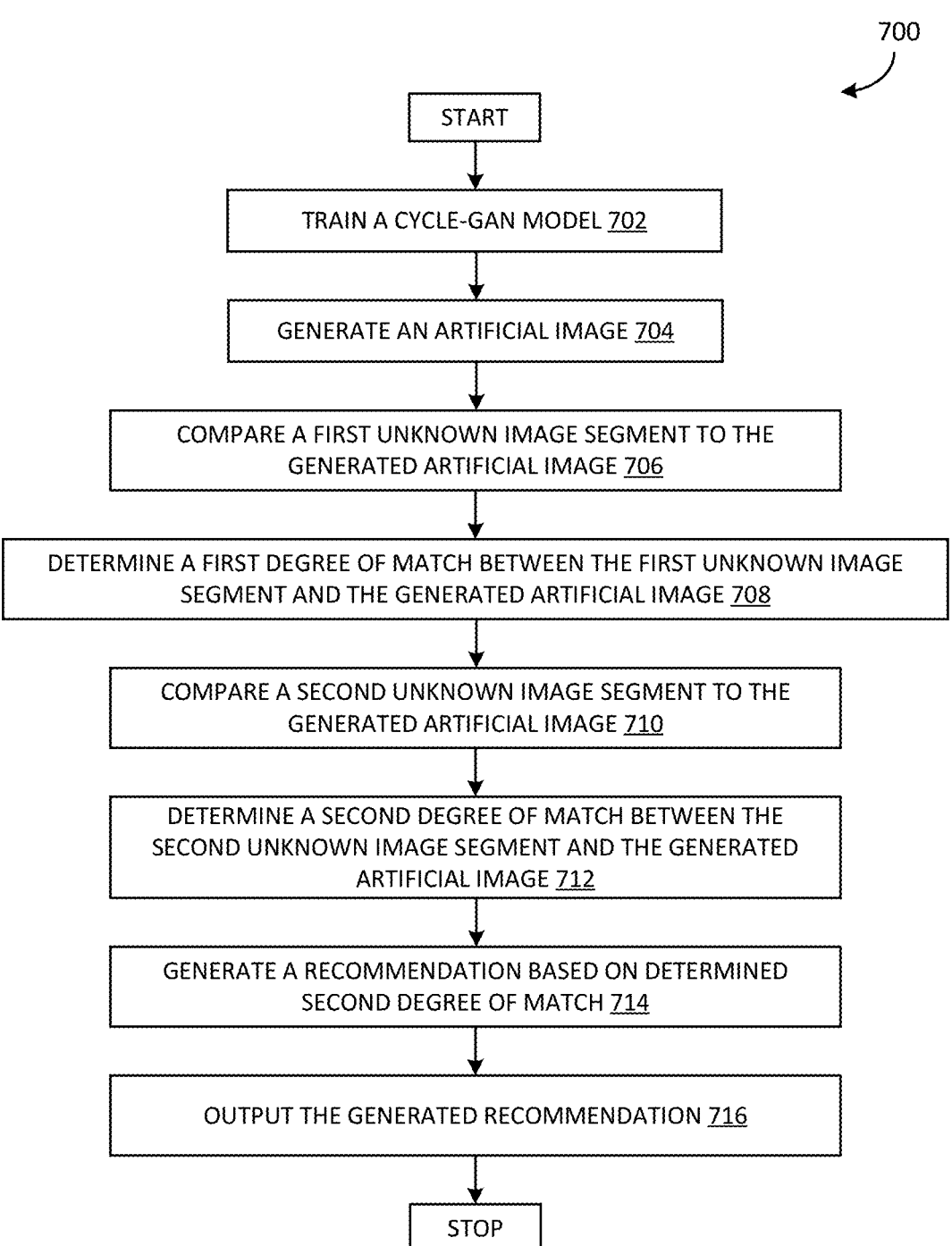
FIG. 7 illustrates an example computer-implemented method of analyzing an image generated by a trained pair of cycle-GAN models.

FIG. 7 illustrates an example computer-implemented method of analyzing an image generated by a trained pair of cycle-GAN models. The computer-implemented method 700 is presented for illustration only and should not be construed as limiting. Other examples of the computer-implemented method 700 can be used without departing from the scope of the present disclosure. The computer-implemented method 700 can be implemented by one or more electronic devices described herein, such as the computing device 302.

The computer-implemented method 700 begins by training a cycle-GAN model, such as the cycle-GAN model complex 317 illustrated in FIG. 3, in operation 702. For example, training the cycle-GAN model may be completed as illustrated and described in operations 508-528 illustrated in FIG. 5. In some examples, the trained cycle-GAN model complex 317 determines an epithelial tissue structure in a real image. In some examples, the real image is initially received from an external device 348 via the communications interface device 312 after being initially acquired by non-invasive or minimally invasive imaging with cellular resolution prior to being received by the communications interface device. Examples of non-invasive or minimally invasive imaging may be selected from a group consisting of reflectance confocal microscopy, fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy.

In operation 704, the image generator 338 generates an artificially generated image using the trained cycle-GAN model complex 317. In some examples, the generated image is an epithelial tissue structure image. The epithelial tissue structure image includes an image segment and is an example of an improved image. For example, the improved epithelial tissue structure image is improved based on the determined epithelial tissue structure. In some examples, the determined epithelial tissue structure includes identified cell coordinates information that is used to extract values of epithelial tissue structure parameters. To generate the image, the image generator 338 extracts values of cell geometry and cell topology parameters from the cell coordinates information. In some examples, the parameters are selected from cell area, perimeter, cell density, distribution of nearest neighbors, and distributions of distances between neighbors.

In operation 706, the image analyzer 342 compares a first unknown image segment to the artificially generated image that is generated in operation 704. In some examples, the first unknown image segment is an image segment of an area of skin. In some examples, the comparison results in a similarity score between the first unknown image segment and the generated image being generated. In operation 708, the image analyzer 342 determines, based on the comparison, a first degree of match between the first unknown image segment and the generated improved epithelial tissue structure image.

In operation 710, the image analyzer 342 receives a second unknown image segment and compares the second unknown image segment to the artificially generated image. In some examples, the comparison results in a similarity score between the second unknown image segment and the artificially generated image. The second unknown image segment is a second image of the area of skin taken after the application of one or more of a skin treatment regimen, ingredient, or composition to the area of the skin for a period of time. In various examples, the period of time of the application may be between one minute and four weeks, between five minutes and twenty-four hours, at least seven days, at least twenty-one days, or any other suitable time period for application. In various examples, the skin treatment regimen, ingredient, or composition enhances one or more attributes selected from a group consisting of reduction of visual dryness, reduction of trans-epidermal water loss, and increase in skin hydration.

In operation 712, based on the comparison, the image analyzer 342 determines a second degree of match between the second unknown image segment and the generated improved epithelial tissue structure image.

In operation 714, the image analyzer 342 generates a recommendation based on the determined second degree of match. The generated recommendation includes the determination of the degree of match between the second unknown image segment and the generated improved epithelial tissue structure image and a determination of whether the applied skin treatment regimen, ingredient, or composition is of benefit to the skin based on the second degree of match being greater than the first degree of match. For example, the image analyzer 342 may determine the applied skin treatment regimen, ingredient, or composition is of benefit to the skin based on a confidence level that the second degree of match is greater than the first degree of match. In some examples, the confidence level is greater than 90%, greater than 80%, or any other suitable confidence level.

In operations 716, the image analyzer 342 outputs the generated recommendation. In some examples, the generated recommendation is output to an external device 348 via the communications interface device 312. In other examples, the generated recommendation is presented on the computing device 302, such as via the user interface device 310. Following operation 716, the computer-implemented method 700 ends.

Figure 8:
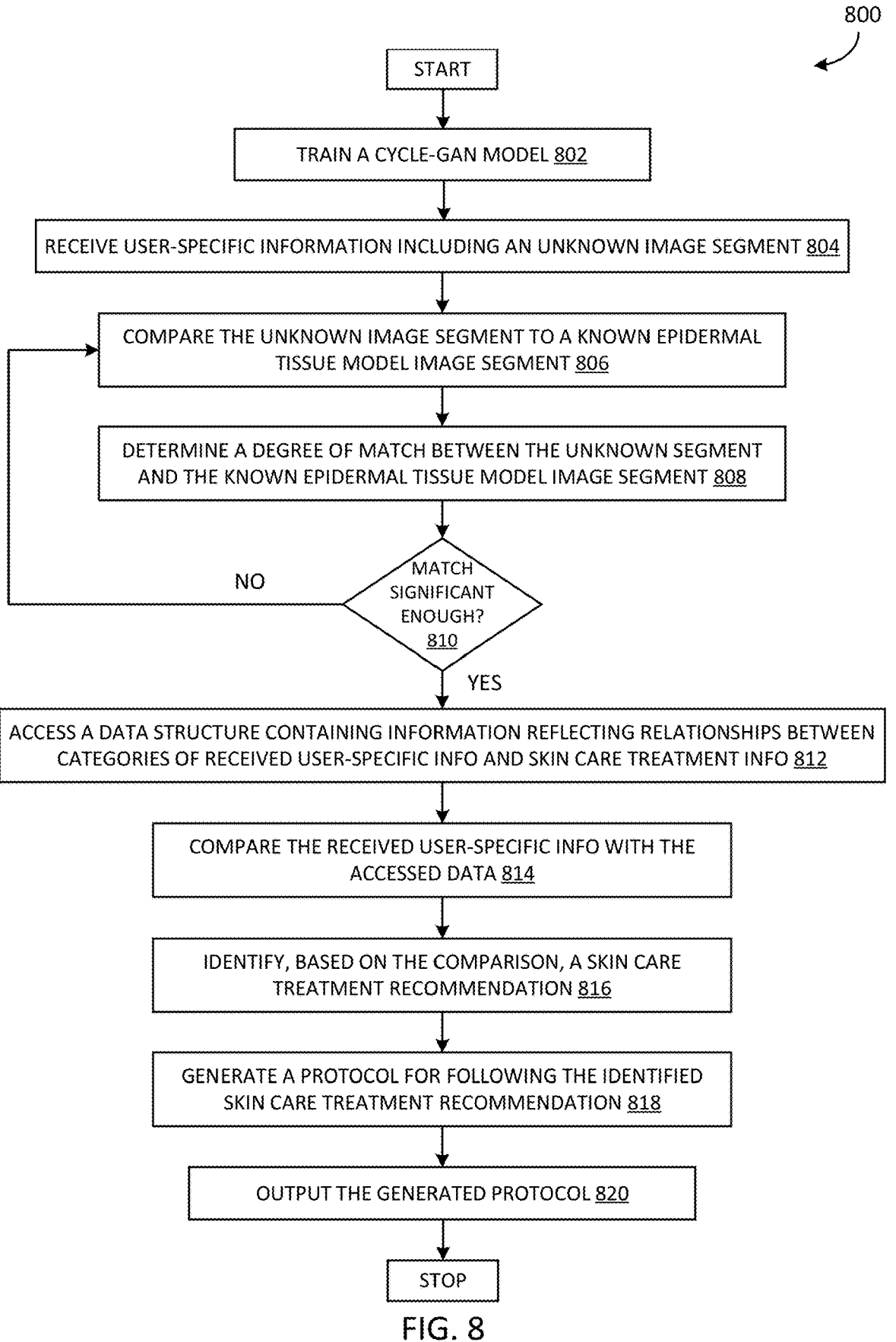
FIG. 8 illustrates an example computer-implemented method of generating a protocol for a skin care treatment recommendation according to various examples.

FIG. 8 illustrates an example computer-implemented method of generating a protocol for a skin care treatment recommendation according to various examples. The computer-implemented method 800 is presented for illustration only and should not be construed as limiting. Other examples of the computer-implemented method 800 can be used without departing from the scope of the present disclosure. The computer-implemented method 800 can be implemented by one or more electronic devices described herein, such as the computing device 302.

The computer-implemented method 800 begins by training a cycle-GAN model, such as the cycle-GAN model complex 317 illustrated in FIG. 3, in operation 802. For example, training the cycle-GAN model may be completed as illustrated and described in operations 508-528 illustrated in FIG. 5 and operation 702 in FIG. 7.

In operation 804, the image analyzer 342 receives user-specific information. The user-specific information may be received from an external device, such as the server 344 or the external device 348. The user-specific information includes an unknown image segment of interest captured by an image capturing device. In some examples, the unknown image segment of interest is analogous to, or similar to, a known epidermal tissue structure model image segment generated by the trained cycle-GAN model complex 317.

In operation 806, the image analyzer 342 compares the unknown image segment to the known epidermal tissue model segment. In some examples, the comparison results in a similarity score between the unknown image segment to the known epidermal tissue model segment being generated. In operation 808, based on the comparison and resulting similarity score, the image analyzer 342 determines a degree of match between the unknown segment and the known epidermal tissue structure model image segment.

In operation 810, the image analyzer 342 determines whether the determined degree of match is significant enough to determine the unknown image segment matches the known epidermal tissue model image segment. In some examples, the image analyzer 342 compares the determined degree of match to a predetermined threshold. In various examples, the threshold may be predetermined, i.e., the degree of match must be greater than a certain percentage such as 90%, 95%, and so forth, or the threshold may be dynamic. For example, the threshold may be dynamic so as to set a different threshold for different types of known epidermal tissue segments. Some types of known epidermal tissue segments may represent types of tissue that are similar enough even if a lower percentage match, such as 80% or 85%, is determined, this percentage indicates a similar or the same treatment recommendation for the type of tissue.

In operation 812, based on the degree of match being greater than the threshold, the image analyzer 342 accesses a data structure, such as the server 344 or the data storage device 314, containing data 314, or information, reflecting relationships between categories of the received user-specific information and skin care treatment information. In some examples, the information reflects relationships derived from known epidermal tissue structure model image segments for skin care treatment.

In operation 814, the image analyzer 342 compares the received user-specific information with the accessed data and in operation 816, identifies, based on the comparison, a skin care treatment recommendation for a user associated with the received user-specific information. In other words, the image analyzer 342 uses the user-specific information and determined image segment of the unknown segment to identify a recommendation for treating the type of skin identified in the unknown image segment. In some examples, the identified recommendation includes a single treatment recommendation. In other examples, the identified recommendation includes more than one treatment recommendation, such as two or three recommendations, that may be implemented to address challenges with the type of skin identified in the unknown image segment.

In operation 818, the image analyzer 342 generates a protocol for following the identified skin care treatment recommendation. In some examples, the generated protocol includes at least one of a test skin treatment regimen, ingredient, or composition. In some examples, the skin treatment regimen, ingredient, or composition enhances one or more attributes selected from a group consisting of reduction of visual dryness, reduction of trans-epidermal water loss, and increase in skin hydration. In some examples, the skin treatment regimen, ingredient, or composition is recommended to be left in contact with skin of the user for an application time between about 1 minute to about 4 weeks. For example, the application time may be at least seven days, may be at least fourteen days, may be at least twenty-one days, and so forth. In another example, the application time may be less than seven days, such as between one minute and twenty-four hours, or between five minutes and about twenty-four hours. In operation 820, the generated protocol is output. In some examples, the generated protocol is output to an external device 348 via the communications interface device 312. In other examples, the generated protocol is presented on the computing device 302, such as via the user interface device 310. Following operation 820, the computer-implemented method 800 ends.

Figure 9:
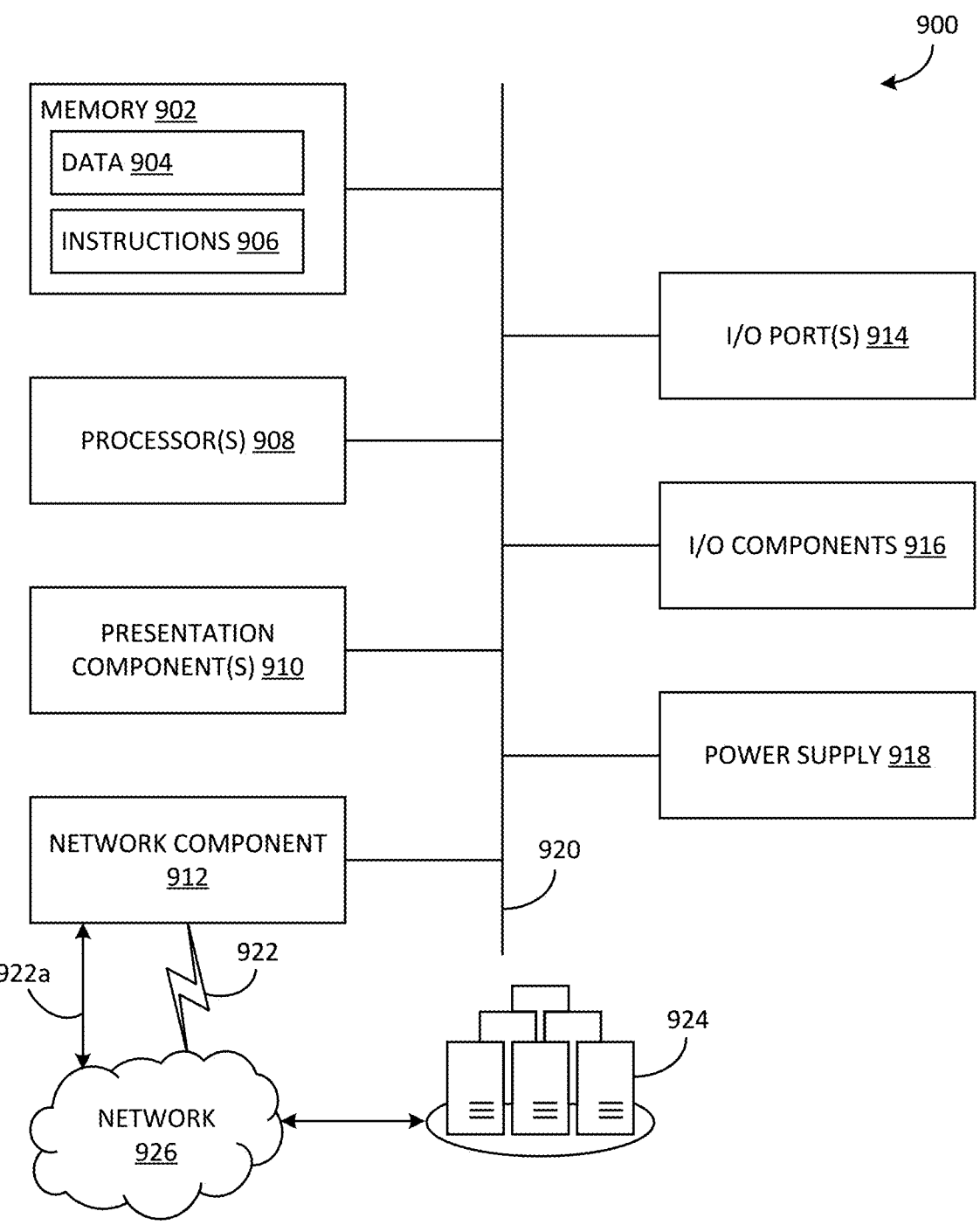
FIG. 9 is a block diagram illustrating an example computing environment suitable for implementing one or more of the various examples disclosed herein.

FIG. 9 is a block diagram illustrating an example computing environment suitable for implementing one or more of the various examples disclosed herein. Computing device 900 is an example of a suitable computing environment and is not intended to suggest any limitation as to the scope of use or functionality of the examples disclosed herein. Neither should computing device 900 be interpreted as having any dependency or requirement relating to any one or combination of components/modules illustrated. The examples disclosed herein may be described in the general context of computer code or machine-useable instructions, including computer-executable instructions such as program components, being executed by a computer or other machine, such as a personal data assistant or other handheld device. Generally, program components including routines, programs, objects, components, data structures, and the like, refer to code that performs particular tasks, or implement particular abstract data types. The disclosed examples may be practiced in a variety of system configurations, including personal computers, laptops, smart phones, mobile tablets, hand-held devices, consumer electronics, specialty computing devices, etc. The disclosed examples may also be practiced in distributed computing environments when tasks are performed by remote-processing devices that are linked through a communications network.

Computing device 900 includes a bus 920 that directly or indirectly couples the following devices: computer-storage memory 902, one or more processors 908, one or more presentation components 910, I/O ports 914, I/O components 916, a power supply 918, and a network component 912. While computing device 900 is depicted as a seemingly single device, multiple computing devices 900 may work together and share the depicted device resources. For example, memory 902 may be distributed across multiple devices, and processor(s) 908 may be housed with different devices.

Bus 920 represents what may be one or more busses (such as an address bus, data bus, or a combination thereof). Although the various blocks of FIG. 7 are shown with lines for the sake of clarity, delineating various components may be accomplished with alternative representations. For example, a presentation component such as a display device is an I/O component in some examples, and some examples of processors have their own memory. Distinction is not made between such categories as "workstation," "server," "laptop," "hand-held device," etc., as all are contemplated within the scope of FIG. 7 and the references herein to a "computing device." Memory 902 may take the form of the computer-storage media references below and operatively provide storage of computer-readable instructions, data structures, program modules and other data for computing device 900. In some examples, memory 902 stores one or more of an operating system, a universal application platform, or other program modules and program data. Memory 902 is thus able to store and access data 904 and instructions 906 that are executable by processor 908 and configured to carry out the various operations disclosed herein.

In some examples, memory 902 includes computer-storage media in the form of volatile and/or nonvolatile memory, removable or non-removable memory, data disks in virtual environments, or a combination thereof. Memory 902 may include any quantity of memory associated with or accessible by computing device 900. Memory 902 may be internal to computing device 900 (as shown in FIG. 7), external to computing device 900, or both. Examples of memory 902 include, without limitation, random access memory (RAM); read only memory (ROM); electronically erasable programmable read only memory (EEPROM); flash memory or other memory technologies; CD-ROM, digital versatile disks (DVDs) or other optical or holographic media; magnetic cassettes, magnetic tape, magnetic disk storage or other magnetic storage devices; memory wired into an analog computing device; or any other medium for encoding desired information and for access by computing device 900. Additionally, or alternatively, memory 902 may be distributed across multiple computing devices 900, for example, in a virtualized environment in which instruction processing is carried out on multiple computing devices 900. For the purposes of this disclosure, "computer storage media," "computer-storage memory," "memory," and "memory devices" are synonymous terms for computer-storage memory 902, and none of these terms include carrier waves or propagating signaling.

Processor(s) 908 may include any quantity of processing units that read data from various entities, such as memory 902 or I/O components 916 and may include CPUs and/or GPUs. Specifically, processor(s) 908 are programmed to execute computer-executable instructions for implementing aspects of the disclosure. The instructions may be performed by the processor, by multiple processors within computing device 900, or by a processor external to client computing device 900. In some examples, processor(s) 908 are programmed to execute instructions such as those illustrated in the in the accompanying drawings. Moreover, in some examples, processor(s) 908 represent an implementation of analog techniques to perform the operations described herein. For example, the operations may be performed by an analog client computing device 900 and/or a digital client computing device 900. Presentation component(s) 910 present data indications to a user or other device. Exemplary presentation components include a display device, speaker, printing component, vibrating component, etc. One skilled in the art will understand and appreciate that computer data may be presented in a number of ways, such as visually in a graphical user interface (GUI), audibly through speakers, wirelessly between computing devices 900, across a wired connection, or in other ways. I/O ports 914 allow computing device 900 to be logically coupled to other devices including I/O components 916, some of which may be built in. Example I/O components 916 include, for example but without limitation, a microphone, joystick, game pad, satellite dish, scanner, printer, wireless device, etc.

Computing device 900 may operate in a networked environment via network component 912 using logical connections to one or more remote computers. In some examples, network component 912 includes a network interface card and/or computer-executable instructions (e.g., a driver) for operating the network interface card. Communication between computing device 900 and other devices may occur using any protocol or mechanism over any wired or wireless connection. In some examples, network component 912 is operable to communicate data over public, private, or hybrid (public and private) using a transfer protocol, between devices wirelessly using short range communication technologies (e.g., near-field communication (NFC), Bluetooth™ branded communications, or the like), or a combination thereof. Network component 912 communicates over wireless communication link 922 and/or a wired communication link 922a to a cloud resource 924 across network 926. Various different examples of communication links 922 and 922a include a wireless connection, a wired connection, and/or a dedicated link, and in some examples, at least a portion is routed through the internet.

Although described in connection with an example computing device 900, examples of the disclosure are capable of implementation with numerous other general-purpose or special-purpose computing system environments, configurations, or devices. Examples of well-known computing systems, environments, and/or configurations that may be suitable for use with aspects of the disclosure include, but are not limited to, smart phones, mobile tablets, mobile computing devices, personal computers, server computers, hand-held or laptop devices, multiprocessor systems, gaming consoles, microprocessor-based systems, set top boxes, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, virtual reality (VR) devices, augmented reality (AR) devices, mixed reality devices, holographic device, and the like. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions, or the specific components or modules illustrated in the figures and described herein. Other examples of the disclosure may include different computer-executable instructions or components having more or less functionality than illustrated and described herein. In examples involving a general-purpose computer, aspects of the disclosure transform the general-purpose computer into a special-purpose computing device when configured to execute the instructions described herein.

By way of example and not limitation, computer readable media comprise computer storage media and communication media. Computer storage media include volatile and nonvolatile, removable and non-removable memory implemented in any method or technology for storage of information such as computer readable instructions, data structures, program modules, or the like. Computer storage media are tangible and mutually exclusive to communication media. Computer storage media are implemented in hardware and are non-transitory, i.e., exclude carrier waves and propagated signals. Computer storage media for purposes of this disclosure are not signals per se. Exemplary computer storage media include hard disks, flash drives, solid-state memory, phase change random-access memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that may be used to store information for access by a computing device. In contrast, communication media typically embody computer readable instructions, data structures, program modules, or the like in a modulated data signal such as a carrier wave or other transport mechanism and include any information delivery media.

In some examples, a computer-implemented method is provided. The computer-implemented method includes training a first cycle-GAN model, wherein the first cycle-GAN model comprises a first generator GB2A, a second generator GA2B, a first discriminator DA, and a second discriminator DB1. Training the first cycle-GAN model comprises receiving, by the first generator GB2A, a real image as a first input, generating, by the first generator GB2A, a first synthetic image as a first output, receiving, by the first discriminator DA, the real image and the first synthetic image from the first generator GB2A, informing, by the first discriminator DA, a likelihood of each of the real image and the first synthetic image as being real or synthetic, receiving, by the second generator GA2B, the real image and the first synthetic image, generating, by the second generator GA2B, a first filtered synthetic image, receiving, by the second discriminator DB1, the real image and the first filtered synthetic image from the second generator GA2B, and informing, by the second discriminator DB1, a likelihood of each of the real image and the first filtered synthetic image as being real or synthetic, wherein the first cycle-GAN model learns noise through learning a translation from the first real image towards binary segmentations. The computer-implemented method further includes training a second cycle-GAN model, wherein the second cycle-GAN model comprises a first generator GC2B, a second generator GB2C, a first discriminator DC, and a second discriminator DB2. Training the second cycle-GAN model comprises receiving, by the first generator GC2B, a Gabor-filtered image as a second input, generating, by the first generator GC2B, a second synthetic image as a second output, receiving, by the first discriminator DC, the Gabor-filtered and the second synthetic image from the first generator GC2B, informing, by the first discriminator DC, a likelihood of each of the Gabor-filtered and the second synthetic image as being Gabor-filtered or synthetic, receiving, by the second generator GB2C, the Gabor-filtered image and the second synthetic image, generating, by the second generator GB2C, a second filtered synthetic image, receiving, by the second discriminator DB2, the Gabor-filtered image and the second filtered synthetic image from the second generator GB2C, and informing, by the second discriminator DB2, a likelihood of each of the Gabor-filtered image and the second filtered synthetic image as being Gabor-filtered or synthetic, wherein the second cycle-GAN model learns a structure of at least one of the real image or the Gabor-filtered image through learning a translation from the Gabor-filtered image towards binary segmentation.

In some examples, a system is provided. The system includes a memory, a processor coupled to the memory, a trained cycle-GAN model, implemented on the processor, configured to determine an epithelial tissue structure in a real image, an image generator, implemented on the processor, configured to generate an improved epithelial tissue structure image based on the determined epithelial tissue structure, and an image analyzer implemented on the processor. The image analyzer is configured to determine, by comparing a first unknown image segment to the generated improved epithelial tissue structure image, a first degree of match between the first unknown image segment and the generated improved epithelial tissue structure image, wherein the first unknown image segment is an image segment of an area of skin, in response to an application of a skin treatment regimen, ingredient, or composition to the area of the skin for a period of time, compare a second unknown image segment to the generated improved epithelial tissue structure image, and determine, based on the comparison, a second degree of match between the second unknown image segment and the generated improved epithelial tissue structure image.

In some examples, one or more non-transitory computer readable medium storing instructions is provided. The instructions, when executed by a processor, cause the processor to receive user-specific information, wherein the user-specific information includes an unknown image segment of interest, and wherein the image segment of interest is analogous to a known epidermal tissue structure model image segment generated by a trained cycle-GAN model; determine, by comparing the unknown image segment to a known epidermal tissue structure model image segment, a degree of match between the unknown segment and the known epidermal tissue structure model image segment; access a data structure containing information reflecting relationships between categories of the received user-specific information and skin care treatment information, wherein the information reflects relationships derived from known epidermal tissue structure model image segments for skin care treatment; compare the received user-specific information with the accessed data; identify, based on the comparison, a skin care treatment recommendation for a user associated with the received user-specific information; generate a protocol for following the identified skin care treatment recommendation; and output the generated protocol.

Further examples for are described herein.

Various examples further include one or more of the following:

wherein at least one of the real image, the Gabor-filtered image, the first synthetic image, or the second synthetic image is an epithelial structure image;

wherein the learned structure learned by the second cycle-GAN includes a position and integrity of membranes of the epithelial structure image;

the position and integrity of membranes of the epithelial structure image include cell coordinates information;

learning the structure of at least one of the real image or the Gabor-filtered image includes extracting values of epithelial tissue structure parameters;

wherein the epithelial tissue structure parameters are selected from cell area, perimeter, cell density, distribution of nearest neighbors, and distributions of distances between neighbors;

wherein the real image are acquired by non-invasive or minimally invasive imaging with cellular resolution;

wherein the non-invasive or minimally invasive imaging is selected from a group consisting of reflectance confocal microscopy, fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy;

wherein the image analyzer is further configured to generate a recommendation including the determination of the degree of match between the second unknown image segment and the generated improved epithelial tissue structure image;

wherein the first unknown image segment is an image of the area of the skin prior to the application of the skin treatment regimen, ingredient, or composition to area of the skin, and the second unknown image segment is an image of the area of the skin after the application of the skin treatment regimen, ingredient, or composition to area of the skin;

wherein the image analyzer is further configured to determine the applied skin treatment regimen, ingredient, or composition is of benefit to the skin based on the second degree of match being greater than the first degree of match;

wherein the image analyzer is further configured to determine the applied skin treatment regimen, ingredient, or composition is of benefit to the skin based on a confidence level of greater than 90% that the second degree of match is greater than the first degree of match;

wherein the determined epithelial tissue structure includes identified cell coordinates information;

wherein the identified cell coordinates information is used to extract values of epithelial tissue structure parameters;

wherein the image generator is configured to extract values of cell geometry and cell topology parameters from the cell coordinates information;

wherein the parameters are selected from cell area, perimeter, cell density, distribution of nearest neighbors, and distributions of distances between neighbors;

further comprising a communications interface device configured to receive the real image from an external device, wherein the real image is acquired by non-invasive or minimally invasive imaging with cellular resolution prior to being received by the communications interface device;

wherein the non-invasive or minimally invasive imaging is selected from a group consisting of reflectance confocal microscopy, fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy;

wherein the generated protocol includes at least one of a test skin treatment regimen, ingredient, or composition to be left in contact with skin of the user for an application time between about 1 minute to about 4 weeks;

wherein the application time is at least 7 days;

wherein the application time is at least about 21 days;

wherein the application time is between about 5 minutes and about 24 hours; and wherein the skin treatment regimen, ingredient, or composition enhances one or more attributes selected from a group consisting of reduction of visual dryness, reduction of trans-epidermal water loss, and increase in skin hydration.

The order of execution or performance of the operations in examples of the disclosure illustrated and described herein is not essential and may be performed in different sequential manners in various examples. For example, it is contemplated that executing or performing a particular operation before, contemporaneously with, or after another operation is within the scope of aspects of the disclosure. When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The invention claimed is:

1. A computer-implemented method, comprising:

training a first cycle-GAN model, wherein the first cycle-GAN model comprises a first generator GB2A, a second generator GA2B, a first discriminator DA, and a second discriminator DB1, and wherein training the first cycle-GAN model comprises:

receiving, by the first generator GB2A, a real image as a first input, generating, by the first generator GB2A, a first synthetic image as a first output, receiving, by the first discriminator DA, the real image and the first synthetic image from the first generator GB2A, informing, by the first discriminator DA, a likelihood of each of the real image and the first synthetic image as being real or synthetic, receiving, by the second generator GA2B, the real image and the first synthetic image, generating, by the second generator GA2B, a first filtered synthetic image, receiving, by the second discriminator DB1, the real image and the first filtered synthetic image from the second generator GA2B, and informing, by the second discriminator DB1, a likelihood of each of the real image and the first filtered synthetic image as being real or synthetic, wherein the first cycle-GAN model learns noise through learning a translation from the first real image towards a first binary segmentation; and training a second cycle-GAN model, wherein the second cycle-GAN model comprises a first generator GC2B, a second generator GB2C, a first discriminator DC, and a second discriminator DB2, and wherein training the second cycle-GAN model comprises:

receiving, by the first generator GC2B, a Gabor-filtered image as a second input, generating, by the first generator GC2B, a second synthetic image as a second output, wherein the second output depends on the first output, receiving, by the first discriminator DC, the Gabor-filtered and the second synthetic image from the first generator GC2B, informing, by the first discriminator DC, a likelihood of each of the Gabor-filtered and the second synthetic image as being Gabor-filtered or synthetic, receiving, by the second generator GB2C, the Gabor-filtered image and the second synthetic image, generating, by the second generator GB2C, a second filtered synthetic image, receiving, by the second discriminator DB2, the Gabor-filtered image and the second filtered synthetic image from the second generator GB2C, and informing, by the second discriminator DB2, a likelihood of each of the Gabor-filtered image and the second filtered synthetic image as being Gabor-filtered or synthetic, wherein the second cycle-GAN model learns a structure of at least one of the real image or the Gabor-filtered image through learning a translation from the Gabor-filtered image towards a second binary segmentation.

2. The computer-implemented method of claim 1, wherein at least one of the real image, the Gabor-filtered image, the first synthetic image, or the second synthetic image is an epithelial structure image.

3. The computer-implemented method of claim 2, wherein the learned structure learned by the second cycle-GAN includes a position and integrity of membranes of the epithelial structure image.

4. The computer-implemented method of claim 3, wherein:

the position and integrity of membranes of the epithelial structure image include cell coordinates information, and learning the structure of at least one of the real image or the Gabor-filtered image includes extracting values of epithelial tissue structure parameters.

5. The computer-implemented method of claim 4, wherein the epithelial tissue structure parameters are selected from cell area, perimeter, cell density, distribution of nearest neighbors, and distributions of distances between neighbors.

6. The computer-implemented method of claim 1, wherein the real image are acquired by non-invasive or minimally invasive imaging with cellular resolution.

7. The computer-implemented method of claim 6, wherein the non-invasive or minimally invasive imaging is selected from a group consisting of reflectance confocal microscopy, fluorescence confocal microscopy, fluorescence lifetime microscopy, multiphoton fluorescence microscopy, second harmonic generation microscopy, chemiluminescence imaging, photoacoustic microscopy, magnetic resonance imaging, optical coherence tomography, line-field optical coherence tomography and photo-thermal microscopy.

\* \* \* \* \*